US012761148B2

(12) United States Patent
Hwang et al.

(10) Patent No.: US 12,761,148 B2
(45) Date of Patent: Oct. 13, 2026

(54) METHOD FOR INSPECTING DISPLAY PANEL AND DISPLAY DEVICE

(71) Applicant: Samsung Display Co., LTD., Yongin-si (KR)

(72) Inventors: Tae Jin Hwang, Yongin-si (KR); Il Woon Kim, Yongin-si (KR); Jang Ki Baek, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 248 days.

(21) Appl. No.: 18/781,160

(22) Filed: Jul. 23, 2024

(65) Prior Publication Data

US 2025/0164394 A1 May 22, 2025

(30) Foreign Application Priority Data

Nov. 17, 2023 (KR) ........................ 10-2023-0159865

(51) Int. Cl.

*B32B 41/00* (2006.01)
*G01N 21/55* (2014.01)
*G01N 33/00* (2006.01)
*G01N 21/95* (2006.01)

(52) U.S. Cl.

CPC ......... *G01N 21/55* (2013.01); *G01N 33/0078* (2024.05); *G01N 2021/9513* (2013.01)

(58) Field of Classification Search

CPC ............... G01N 21/55; G01N 33/0078; G01N 2021/9513; G01N 21/95; G09G 3/006; G09G 2330/04; H10K 59/131; H10K 71/70; H10K 59/1213; H10K 59/126; H10K 59/873; H10K 59/8791; H10K 59/88;

(Continued)

(56) References Cited

U.S. PATENT DOCUMENTS

| | | | | |
|---|---|---|---|---|
| 10,403,703 | B2 | 9/2019 | Yamazaki | |
| 2009/0219521 | A1 * | 9/2009 | Shin | G02F 1/1309 356/239.2 |
| 2018/0188189 | A1 | 7/2018 | Hwang | |

FOREIGN PATENT DOCUMENTS

| | | | |
|---|---|---|---|
| KR | 10-2017-0020854 | A | 2/2017 |
| KR | 10-1754517 | | 7/2017 |
| KR | 10-2072061 | | 2/2020 |

* cited by examiner

*Primary Examiner* — Michael N Orlando
*Assistant Examiner* — Joshel Rivera
(74) *Attorney, Agent, or Firm* — Womble Bond Dickinson (US) LLP

(57) ABSTRACT

A method for inspecting a display device includes forming a backplane, an organic light-emitting layer, an encapsulation layer and a polarizing film in a display area, bonding a driver circuit to a non-display area and covering the driver circuit by a protective layer, applying a shielding resin between the polarizing film and the protective layer, and applying a test pattern made of a same material as the shielding resin to a dummy area of the non-display area, irradiating the test pattern with ultraviolet light using a lighting device, and determining an angle and a light amount of the lighting device that make the ultraviolet light reflected from the test pattern to satisfy a specified optical condition, irradiating the shielding resin with ultraviolet light based on the determined angle and light amount, and determining whether the shielding resin is properly applied by analyzing ultraviolet light reflected from the shielding resin.

20 Claims, 14 Drawing Sheets

(58) Field of Classification Search
CPC . H10K 77/111; G01M 11/0278; G01J 1/0228; G01J 1/429; G01J 2001/4247; G09F 9/301
USPC .................... 156/60, 64, 350, 351, 378, 379
See application file for complete search history.

DU : SUB, TFTL, EML, TFEL

METHOD FOR INSPECTING DISPLAY PANEL AND DISPLAY DEVICE

CROSS REFERENCE TO RELATED APPLICATION(S)

This application claims priority to and benefits of Korean Patent Application No. 10-2023-0159865 under 35 U.S.C. § 119, filed on Nov. 17, 2023, in the Korean Intellectual Property Office, the entire contents of which are incorporated herein by reference.

BACKGROUND

1. Technical Field

Embodiments relate to a method for inspecting display panels and display devices.

2. Description of the Related Art

As the information-oriented society evolves, various demands for display devices are increasing. Light-emitting display devices may include an organic light-emitting display device including organic light-emitting emitting diodes as light-emitting elements, or a light-emitting diode display device including inorganic light-emitting diodes such as light-emitting diodes (LEDs) as light-emitting elements.

Display devices are widely employing a display panel using a flexible substrate. A display panel using a flexible substrate may be bent, folded, or rolled, and thus may be applied to electronic devices of various form factors. A display panel using a flexible substrate includes a display area that is substantially flat and displays images, and a non-display area disposed outside the display area, where a driver circuit is bonded. A part of the non-display area may be bent toward the rear side of the display panel in order to reduce the bezel width when the display panel is viewed from the top (or in plan view). The part of the non-display area of the display panel may be covered with a protective layer so that damage may be prevented. In the display panel, a shielding resin is applied at the boundary between a cover area covered by the protective layer and the encapsulation layer of the display area in order to prevent damage to the display panel due to introduction of static electricity. In case that the shielding resin is not properly applied at the boundary between the cover area covered by the protective layer and the encapsulation layer of the display area, damage to the display panel may occur due to introduction of static electricity. In view of the above, what is required is a technique for readily inspecting whether the shielding resin is properly applied.

SUMMARY

Aspects of the disclosure provide a method for inspecting a display panel and a display device that provides convenient and accurate inspection to check whether a shielding resin is properly applied. The shielding resin may prevent damage to the display panel due to the introduction of static electricity.

According to an embodiment, a method for inspecting a display device may include forming a backplane, an organic light-emitting layer, an encapsulation layer and a polarizing film in a display area of a substrate, bonding a driver circuit to a non-display area of the substrate and covering the driver circuit by a protective layer, applying a shielding resin to a boundary area between the polarizing film and the protective layer, and applying a test pattern made of a same material as the shielding resin to a dummy area of the non-display area disposed at an outermost position of the substrate, irradiating the test pattern with ultraviolet light using a lighting device, and determining an angle and a light amount of the lighting device that make the ultraviolet light reflected from the test pattern to satisfy a specified optical condition, irradiating the shielding resin with ultraviolet light based on the determined angle and the determined light amount, and determining whether the shielding resin is properly applied by analyzing ultraviolet light reflected from the shielding resin.

The non-display area may include a bending area that is bent to overlap the display area, wherein the driver circuit is bonded in the bending area. The bending area may include a shielding area where a plurality of fan-out lines extended from the display area to the driver circuit and the shielding resin covering the plurality of fan-out lines are disposed, and the dummy area disposed at each of end portions of the shielding area.

The fan-out lines may not be disposed in the dummy area.

The determining of the angle and the light amount of the lighting device that satisfies the specified optical condition may include setting a plurality of optical conditions as combinations of a plurality of angle conditions related to the angle of the lighting device and a plurality of light amount conditions related to the light amount of the lighting device, irradiating ultraviolet light to the substrate according to each of the optical conditions, and measuring first reflected light reflected from the polarizing film, second reflected light reflected from the test pattern, and third reflected light reflected from the protective layer, calculating an average of the first reflected light and the third reflected light, and calculating a deviation between the second reflected light and the calculated average of the first reflected light and the third reflected light, and calculating the deviation of the second reflected light according to each of the optical conditions, and determining that an optical condition with a smallest deviation of the second reflected light among the optical conditions satisfies the specified optical condition.

The determining of the angle and the light amount of the lighting device that satisfy the specified optical condition is performed for each wafer lot, which is fabricated under same conditions.

The determining of the angle and the light amount of the lighting device that satisfy the specified optical condition is performed for each batch, which is fabricated under same conditions.

The determining of the angle and the light amount of the lighting device that satisfy the specified optical condition is performed for each cell, which is fabricated under same conditions.

The angle conditions related to the angle of the lighting device may be set in a range of about 10 degrees to about 30 degrees.

The light amount conditions related to the light amount of the lighting device may be set in a range of about 10 W to about 30 W.

The determining whether the shielding resin is properly applied may include calculating irregularity of ultraviolet light reflected from the shielding resin, and determining that the shielding resin is not properly applied in case that the irregularity exceeds a reference threshold value.

According to an embodiment, a method for inspecting a display panel may include forming a backplane, an organic light-emitting layer, an encapsulation layer and a polarizing film in a display area of a substrate, bonding a driver circuit to a non-display area of the substrate and covering the driver circuit with a protective layer, applying a shielding resin to a boundary area between the polarizing film and the protective layer, and applying a test pattern made of a same material as the shielding resin to a dummy area of the non-display area disposed at an outermost position of the substrate, irradiating the test pattern with ultraviolet light using a lighting device, and determining an angle and a light amount of the lighting device that make the ultraviolet light reflected from the test pattern to satisfy a specified optical condition, irradiating the shielding resin with ultraviolet light based on the determined angle and the determined light amount, and determining whether the shielding resin is properly applied by analyzing ultraviolet light reflected from the shielding resin.

The non-display area may include a bending area that is bent to overlap the display area, wherein the driver circuit is bonded in the bending area. The bending area may include a shielding area where a plurality of fan-out lines extended from the display area to the driver circuit and the shielding resin covering the plurality of fan-out lines are disposed, and a dummy area disposed at each of end portions of the shielding area.

The fan-out lines may not be disposed in the dummy area.

The determining of the angle and the light amount of the lighting device that satisfies the specified optical condition may include setting a plurality of optical conditions as combinations of a plurality of angle conditions related to the angle of the lighting device and a plurality of light amount conditions related to the light amount of the lighting device, irradiating ultraviolet light to the substrate for each of the optical conditions, and measuring first reflected light reflected from the polarizing film, second reflected light reflected from the test pattern, and third reflected light reflected from the protective layer, calculating an average of the first reflected light and the third reflected light, and calculating a deviation between the second reflected light and the average of the first reflected light and the third reflected light, and calculating the deviation of the second reflected light according to each of the optical conditions, and determining that an optical condition with a smallest deviation of the second reflected light among the optical conditions satisfies the specified optical condition.

The determining of the angle and the light amount of the lighting device that satisfy the specified optical condition is performed for each wafer lot, which is fabricated under same conditions.

The determining of the angle and the light amount of the lighting device that satisfy the specified optical condition is performed for each batch, which is fabricated under same conditions.

The determining of the angle and the light amount of the lighting device that satisfy the specified optical condition is performed for each cell, which is fabricated under same conditions.

The angle conditions related to the angle of the lighting device may be set in a range of about 10 degrees to about 30 degrees.

The light amount conditions related to the light amount of the lighting device may be set in a range of about 10 W to about 30 W.

The determining whether the shielding resin is properly applied may include calculating irregularity of ultraviolet light reflected from the shielding resin, and determining that the shielding resin is not properly applied in case that the irregularity exceeds a reference threshold value.

According to the embodiments of the disclosure, it is possible to easily inspect in case that a shielding resin is properly applied, which prevents damage to a display panel due to introduction of static electricity in a display device.

BRIEF DESCRIPTION OF THE DRAWINGS

The above and other aspects and features of the disclosure will become more apparent by describing in detail embodiments thereof with reference to the attached drawings, in which.

DETAILED DESCRIPTION OF THE EMBODIMENTS

Figure 1:
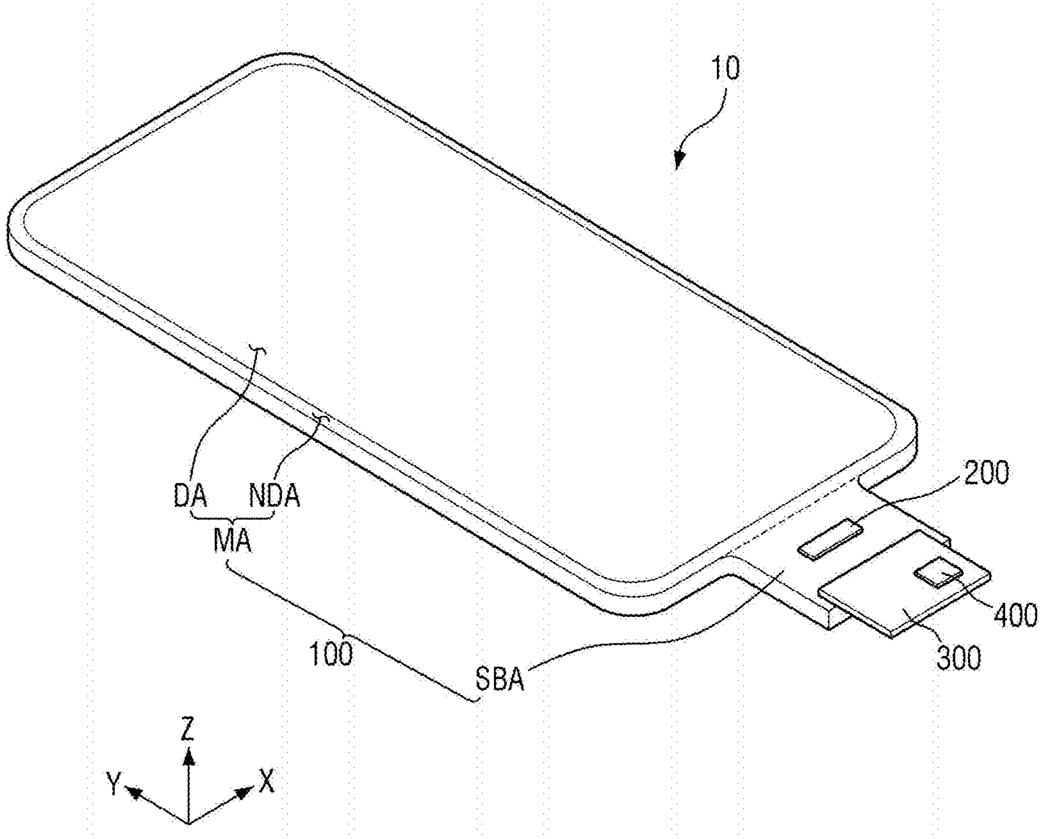
FIG. 1 is a schematic perspective view of a display device according to an embodiment.

In the following description, for the purposes of explanation, numerous specific details are set forth in order to provide a thorough understanding of various embodiments or implementations of the invention. As used herein, "embodiments" and "implementations" are interchangeable words that are non-limiting examples of devices or methods disclosed herein. It is apparent, however, that various embodiments may be practiced without these specific details or with one or more equivalent arrangements. Here, various embodiments do not have to be exclusive nor limit the disclosure. For example, specific shapes, configurations, and characteristics of an embodiment may be used or implemented in another embodiment.

Unless otherwise specified, the illustrated embodiments are to be understood as providing features of the invention. Therefore, unless otherwise specified, the features, components, modules, layers, films, panels, regions, and/or aspects, etc. (hereinafter individually or collectively referred to as "elements"), of the various embodiments may be otherwise combined, separated, interchanged, and/or rearranged without departing from the scope of the invention.

The use of cross-hatching and/or shading in the accompanying drawings is generally provided to clarify boundaries between adjacent elements. As such, neither the presence nor the absence of cross-hatching or shading conveys or indicates any preference or requirement for particular materials, material properties, dimensions, proportions, commonalities between illustrated elements, and/or any other characteristic, attribute, property, etc., of the elements, unless specified. Further, in the accompanying drawings, the size and relative sizes of elements may be exaggerated for clarity and/or descriptive purposes. When an embodiment may be implemented differently, a specific process order may be performed differently from the described order. For example, two consecutively described processes may be performed substantially at the same time or performed in an order opposite to the described order. Also, like reference numerals denote like elements.

When an element or a layer is referred to as being "on," "connected to," or "coupled to" another element or layer, it may be directly on, connected to, or coupled to the other element or layer or intervening elements or layers may be present. When, however, an element or layer is referred to as being "directly on," "directly connected to," or "directly coupled to" another element or layer, there are no intervening elements or layers present. To this end, the term "connected" may refer to physical, electrical, and/or fluid connection, with or without intervening elements. For the purposes of this disclosure, "at least one of A and B" may be understood to mean A only, B only, or any combination of A and B. Also, "at least one of X, Y, and Z" and "at least one selected from the group consisting of X, Y, and Z" may be construed as X only, Y only, Z only, or any combination of two or more of X, Y, and Z. As used herein, the term "and/or" includes any and all combinations of one or more of the associated listed items.

Although the terms "first," "second," etc. may be used herein to describe various types of elements, these elements should not be limited by these terms. These terms are used to distinguish one element from another element. Thus, a first element discussed below could be termed a second element without departing from the teachings of the disclosure.

Spatially relative terms, such as "beneath," "below," "under," "lower," "above," "upper," "over," "higher," "side" (e.g., as in "sidewall"), and the like, may be used herein for descriptive purposes, and, thereby, to describe one element's relationship to another element(s) as illustrated in the drawings. Spatially relative terms are intended to encompass different orientations of an apparatus in use, operation, and/or manufacture in addition to the orientation depicted in the drawings. For example, if the apparatus in the drawings is turned over, elements described as "below" or "beneath" other elements or features would then be oriented "above" the other elements or features. Thus, the term "below" can encompass both an orientation of above and below. Furthermore, the apparatus may be otherwise oriented (e.g., rotated 90 degrees or at other orientations), and, as such, the spatially relative descriptors used herein should be interpreted accordingly.

The terminology used herein is for the purpose of describing particular embodiments and is not intended to be limiting. As used herein, the singular forms, "a," "an," and "the" are intended to include the plural forms as well, unless the context clearly indicates otherwise. Moreover, the terms "comprises," "comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof. It is also noted that, as used herein, the terms "substantially," "about," and other similar terms, are used as terms of approximation and not as terms of degree, and, as such, are utilized to account for inherent deviations in measured, calculated, and/or provided values that would be recognized by one of ordinary skill in the art.

Various embodiments are described herein with reference to sectional and/or exploded illustrations that are schematic illustrations of embodiments and/or intermediate structures. As such, variations from the shapes of the illustrations as a result, for example, of manufacturing techniques and/or tolerances, are to be expected. Thus, embodiments disclosed herein should not necessarily be construed as limited to the particular illustrated shapes of regions, but are to include deviations in shapes that result from, for instance, manufacturing. In this manner, regions illustrated in the drawings may be schematic in nature and the shapes of these regions may not reflect actual shapes of regions of a device and, as such, are not necessarily intended to be limiting.

As customary in the field, some embodiments are described and illustrated in the accompanying drawings in terms of functional blocks, units, and/or modules. Those skilled in the art will appreciate that these blocks, units, and/or modules are physically implemented by electronic (or optical) circuits, such as logic circuits, discrete components, microprocessors, hard-wired circuits, memory elements, wiring connections, and the like, which may be formed using semiconductor-based fabrication techniques or other manufacturing technologies. In the case of the blocks, units, and/or modules being implemented by microprocessors or other similar hardware, they may be programmed and controlled using software (e.g., microcode) to perform various functions discussed herein and may optionally be driven by firmware and/or software. It is also contemplated that each block, unit, and/or module may be implemented by dedicated hardware, or as a combination of dedicated hardware to perform some functions and a processor (e.g., one or more programmed microprocessors and associated circuitry) to perform other functions. Also, each block, unit, and/or module of some embodiments may be physically separated into two or more interacting and discrete blocks, units, and/or modules without departing from the scope of the invention. Further, the blocks, units, and/or modules of some embodiments may be physically combined into more complex blocks, units, and/or modules without departing from the scope of the invention.

Hereinafter, specific embodiments will be described with reference to the accompanying drawings.

Figure 2:
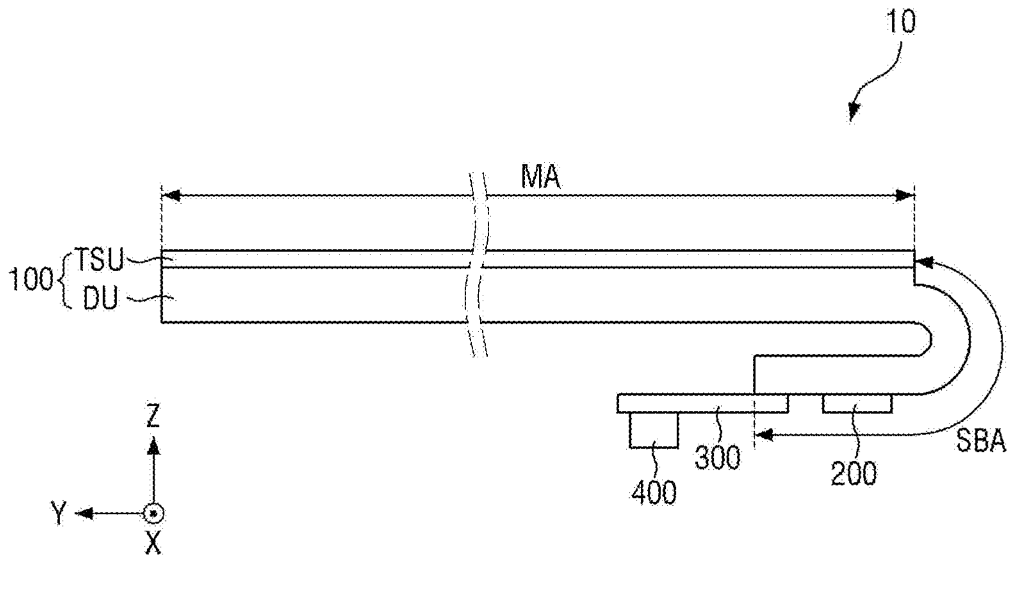
FIG. 2 is a schematic cross-sectional view of the display device according to the embodiment.

FIG. 1 is a schematic plan view of a display device according to an embodiment. FIG. 2 is a schematic cross-sectional view of the display device according to the embodiment.

In the drawings, a first direction X refers to a direction parallel to a side of the display device 10 when viewed from the top (or in plan view), e.g., the shorter side direction of the display device 10. A second direction Y refers to a direction parallel to another side of the display device 10 that meets the side when viewed from the top (or in plan view), e.g., the longer side direction of the display device 10. A third direction Z refers to the thickness direction of the display device 10. It should be understood that the directions referred to in the embodiments are relative directions, and the embodiments are not limited to the directions mentioned.

The display device 10 may include a variety of electronic devices that provide a display screen. For example, the display device 10 may be employed by portable electronic devices such as a mobile phone, a smart phone, a tablet PC, a mobile communications terminal, an electronic notebook, an electronic book, a portable multimedia player (PMP), a navigation device and an ultra mobile PC (UMPC). For example, the display device 10 may be used as a display unit DU of a television, a laptop computer, a monitor, an electronic billboard, or the Internet of Things (IOT). For example, the display device 10 may be applied to wearable devices such as a smart watch, a watch phone, a glasses-type display, and a head-mounted display (HMD) device.

Referring to FIG. 1, the display device 10 may have a shape similar to a rectangle when viewed from the top (or in plan view). For example, the display device 10 may have a shape similar to a quadrangle having shorter sides in the first direction X and longer sides in the second direction Y when viewed from the top (or in plan view). The corners where the shorter sides in the first direction X meet the longer sides in the second direction Y may be rounded at a selected curvature or may be a right angle. The shape of the display device 10 when viewed from the top (or in plan view) is not limited to a rectangular shape, but may have a shape similar to other polygonal shapes, a circular shape, or an elliptical shape.

At least one of the front surface and the rear surface of the display device 10 may be a display surface. For example, the front surface refers to the surface positioned on a side of a plane, e.g., the surface positioned on the side indicated by the arrow of the third direction Z in the drawings. The rear surface refers to the surface positioned on the opposite side of the plane, e.g., the surface positioned on the opposite side to the side indicated by the arrow of the third direction Z in the drawings. The display device 10 may be a double-sided display device 10 in which images are displayed on both the front and rear surfaces. In the following description, the display surface may be positioned on the front side of the display device 10 according to the embodiment.

The display device 10 may include a display panel 100 providing a display screen, a display driver 200, a circuit board 300 and a touch driver 400. The touch driver 400 may be an element that senses a user's touch input and may be referred to as a "touch detection device."

The display panel 100 may have a shape similarly to a rectangular shape when viewed from the top (or in plan view). For example, the display panel 100 may have a shape similar to a quadrangle having shorter sides in the first direction X and longer sides in the second direction Y when viewed from the top. The corners where the shorter sides in the first direction X meet the longer sides in the second direction Y may be rounded at a selected curvature or may be a right angle. The shape of the display panel 100 when viewed from the top (or in plan view) is not limited to a rectangular shape, but may have a shape similar to other polygonal shapes, a circular shape, or an elliptical shape. For example, the display panel 100 may be formed to be flexible so that it may be curved or bent.

The display panel 100 may include a main area MA and a subsidiary area (or bending area) SBA.

The main area MA may include the display area DA including pixels for displaying images, and the non-display area NDA positioned around the display area DA. The display area DA may output lights from emission areas or open areas. For example, the display panel 100 may include a pixel circuit including switching elements, a pixel-defining layer that defines the emission areas or the opening areas, and a self-light-emitting element.

The non-display area NDA may be disposed on the outer side of the display area DA. The non-display area NDA may be defined as the edge portion of the main area MA of the display panel 100. The non-display area NDA may include a gate driver supplying gate signals to gate lines of the display panel 100.

The subsidiary area SBA may extend from a side of the main area MA. The subsidiary area SBA may be bent such that the subsidiary area SBA may overlap the main area MA in the third direction Z. The subsidiary area SBA may include pads connected (e.g., electrically connected) to the display driver 200 and the circuit board 300.

Referring to FIG. 2, the display panel 100 may include a display unit DU and a touch unit TSU.

Figure 3:
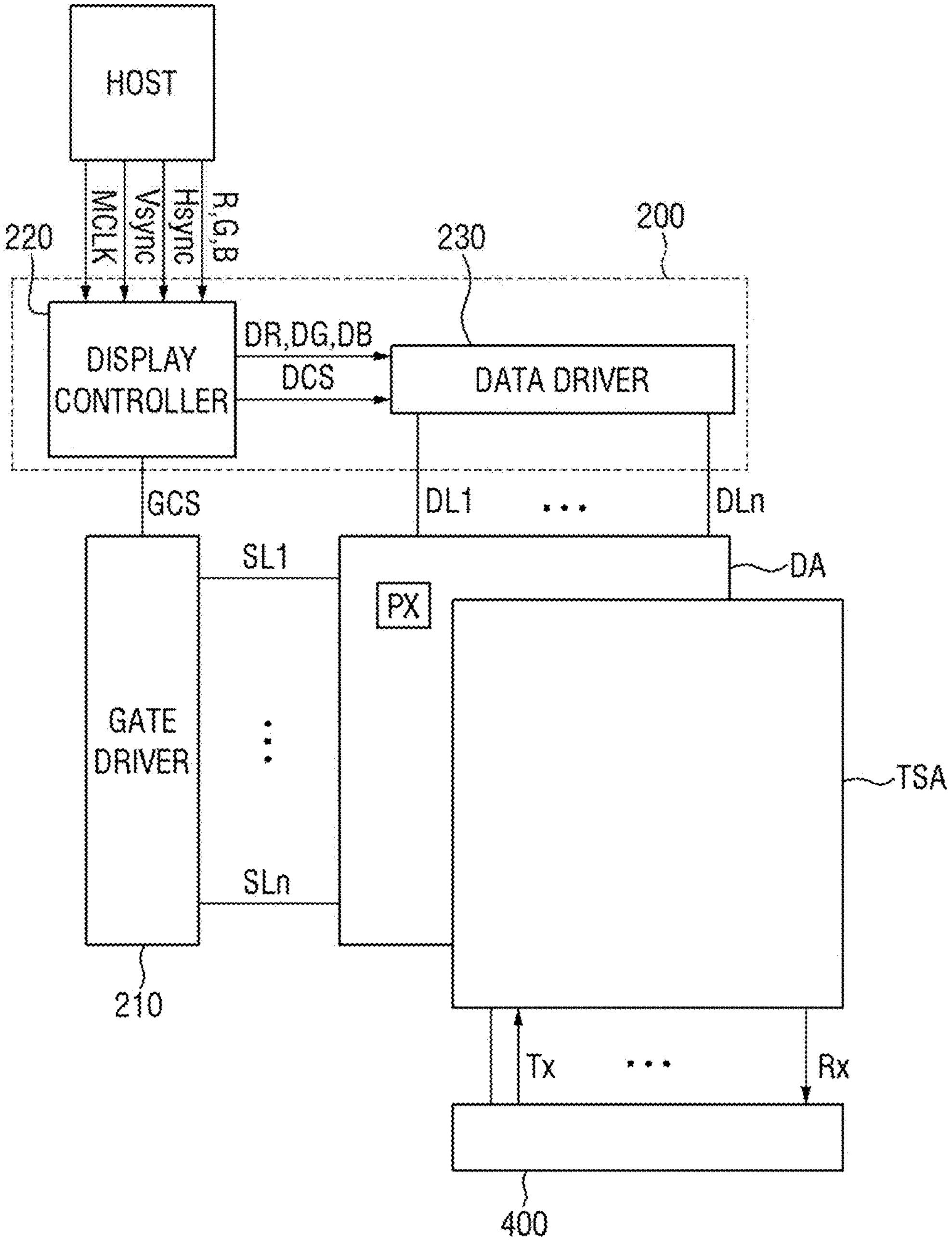
FIG. 3 is a schematic view conceptually showing the display unit and the touch driver according to the embodiment.

The display unit DU may include pixels PX (see FIG. 3). Each of the pixels PX may be a unit for displaying an image. A pixel (e.g., single pixel) PX may include a red sub-pixel, a green sub-pixel, and a blue sub-pixel, but embodiments are not limited thereto. The pixels PX may be arranged alternately when viewed from the top (or in plan view). For example, the pixels PX may be arranged in a matrix, but embodiments are not limited thereto.

The touch unit TSU may be disposed on the display unit DU, but embodiments are not limited thereto. For example, the touch unit TSU may be formed together with the display unit DU using an in-cell touch technology. The touch unit TSU may include touch electrodes SEN (e.g., RE and TE in FIG. 5) for detecting a user's touch by capacitive sensing, touch driving lines TL (see FIG. 5) for connecting driving electrodes TE to the touch driver 400, and touch sensing lines RL for connecting sensing electrodes RE to the touch driver 400 (see FIG. 5). The touch unit TSU may be a layer that detects a touch input and may work as a touch member. The touch unit TSU may determine whether there is a touch input and may calculate touch input coordinates of the position. The display unit DU and the touch unit TSU will be described in detail later with reference to FIGS. 4 to 7.

The display unit DU and the touch unit TSU may overlap each other. For example, the display area DA may display images on the screen and may detect a touch input.

The subsidiary area SBA of the display panel 100 may extend from a side of the main area MA. The subsidiary area SBA may include a flexible material that is bendable, foldable, or rollable. For example, a part of the subsidiary area SBA may be bent on a side of the main area MA, and another part of the subsidiary area SBA extended from the bent part of the subsidiary area SBA may overlap the main area MA in the third direction (e.g., z-axis direction). The subsidiary area SBA may include pads connected (e.g., electrically connected) to the display driver 200 and the circuit board 300.

Referring to FIG. 1, the display driver 200 may be disposed in the subsidiary area SBA of the display panel 100. For example, the display driver 200 may be implemented as an integrated circuit (IC) and may be mounted on the display panel 100 by the chip-on-glass (COG) technique, or the chip-on-plastic (COP) technique.

The display driver 200 may output data signals and voltages for driving the display panel 100. The display driver 200 may supply data voltages to data lines of the display panel 100. The display driver 200 may provide supply voltages to voltage lines of the display panel 100 and may provide gate control signals to the gate driver.

The circuit board 300 may be disposed in the subsidiary area SBA of the display panel 100. Lead lines of the circuit board 300 may be connected (e.g., electrically connected) to the pad area of the display panel 100. The circuit board 300 may be a flexible printed circuit board, a printed circuit board, or a flexible film such as a chip-on film.

The circuit board 300 may include conductive layers that transmits a signal from a main circuit board to the display driver 200 or electrically connects the touch driver 400 with the driving electrodes TE and the sensing electrodes RE of the touch unit TSU.

The touch driver 400 may be disposed in the subsidiary area SBA of the display panel 100. In another example, the touch driver 400 may be mounted on the circuit board 300.

The touch driver 400 may determine whether there is a touch input and may find the coordinates of the touch input by sensing the amount of a change in the capacitance between the touch electrodes SEN. The touch driver 400 may be implemented as an integrated circuit (IC) and may be mounted on the display panel 100 by a chip-on-glass (COG) technique, or a chip-on-plastic (COP) technique.

Figure 4:
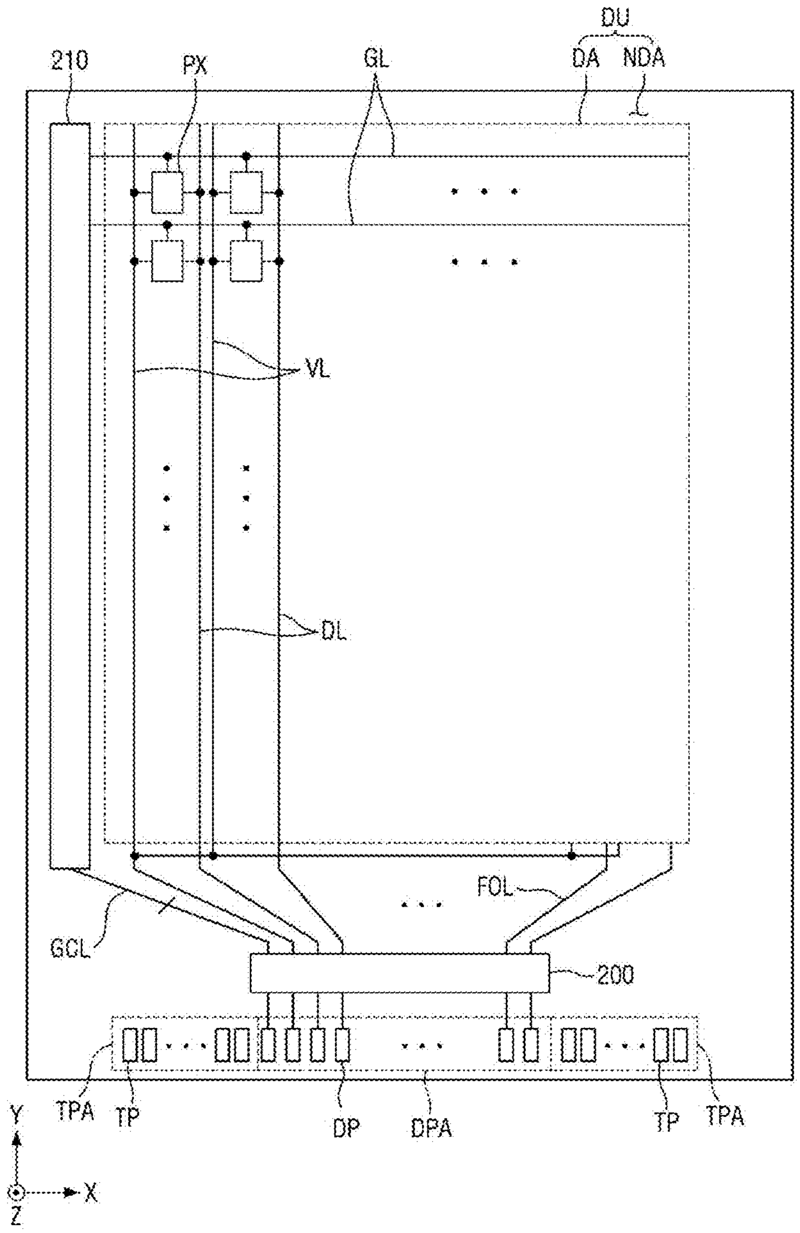
FIG. 4 is a schematic plan view showing the display unit of the display device according to the embodiment.

FIG. 3 is a schematic view conceptually showing the display unit and the touch driver according to the embodiment. FIG. 4 is a schematic plan view showing the display unit of the display device according to the embodiment.

Referring to FIGS. 3 and 4, the display device 10 may include the display panel 100 including pixels PX, the display driver 200 and the touch driver 400.

The display driver 200 may include a data driver 230 and a display controller 220.

The display controller 220 may receive input data R, G and B and timing control signals from an external source (e.g., a host). The timing control signals may include a vertical synchronization signal Vsync indicating one frame period, a horizontal synchronization signal Hsync indicating one horizontal period, and a main clock MCLK repeated at a selected cycle. The input data R, G and B may be RGB data including red image data, green image data, and blue image data. The display controller 220 may generate output data signals DR, DG and DB and internal control signals using the input data R, G and B and the timing control signal. The internal control signal may include a data driver control signal DCS and a gate driver control signal GCS.

The display controller 220 may control the operation of the data driver 230 by providing the data driver control signal DCS to the data driver 230. The display controller 220 may control the operation of the gate driver 210 by providing the gate driver control signal GCS to the gate driver 210.

The data driver 230 may receive the output data signals DR, DG and DB and the data driver control signal DCS from the display controller 220. The data driver 230 may generate a data signal using the output data signals DR, DG and DB and the data driver control signal DCS. The data driver 230 may provide the generated data signal to the display panel 100. The data driver 230 may provide data signals to the pixels PX through data lines DL1 to DLn (DL in FIG. 4) formed in the display panel 100.

The gate driver 210 may receive the gate driver control signal GCS from the display controller 220. The gate driver 210 may generate a gate signal using the received gate driver control signal GCS. The gate driver 210 may provide the generated gate signal to the display panel 100. The gate driver 210 may provide gate signals to the pixels PX through gate lines SL1 to SLn (GL in FIG. 4) formed in the display panel 100. The data lines DL1 to DLn and the gate lines SL1 to SLn will be described in detail later with reference to FIG. 4.

Although the display driver 200 does not include the gate driver 210 in the example shown in FIG. 3, embodiments are not limited thereto. For example, the gate driver 210 may be included in the display driver 200 that controls the operation of the display panel 100. The gate driver 210, the data driver 230 and the display controller 220 may be implemented as integrated circuits (ICs). The gate driver 210 may be formed together during a process of fabricating thin-film transistors of the display panel 100. The display controller 220 and the data driver 230 may be merged to form a timing controller embedded driver (TED) integrated circuit.

The display panel 100 may include pixels PX connected (e.g., electrically connected) to the data lines DL (see FIG. 4) and the gate lines GL (see FIG. 4).

A frame frequency at which the display driver 200 drives the display panel 100 may be variable. For example, the frame frequency may vary within the range of about 1 Hz to about 240 Hz pursuant to a host or a user's selection. The display driver 200 may drive the display panel 100 at about 60 Hz for one period and may change the frame frequency to about 120 Hz for another period pursuant to a user's needs.

Figure 5:
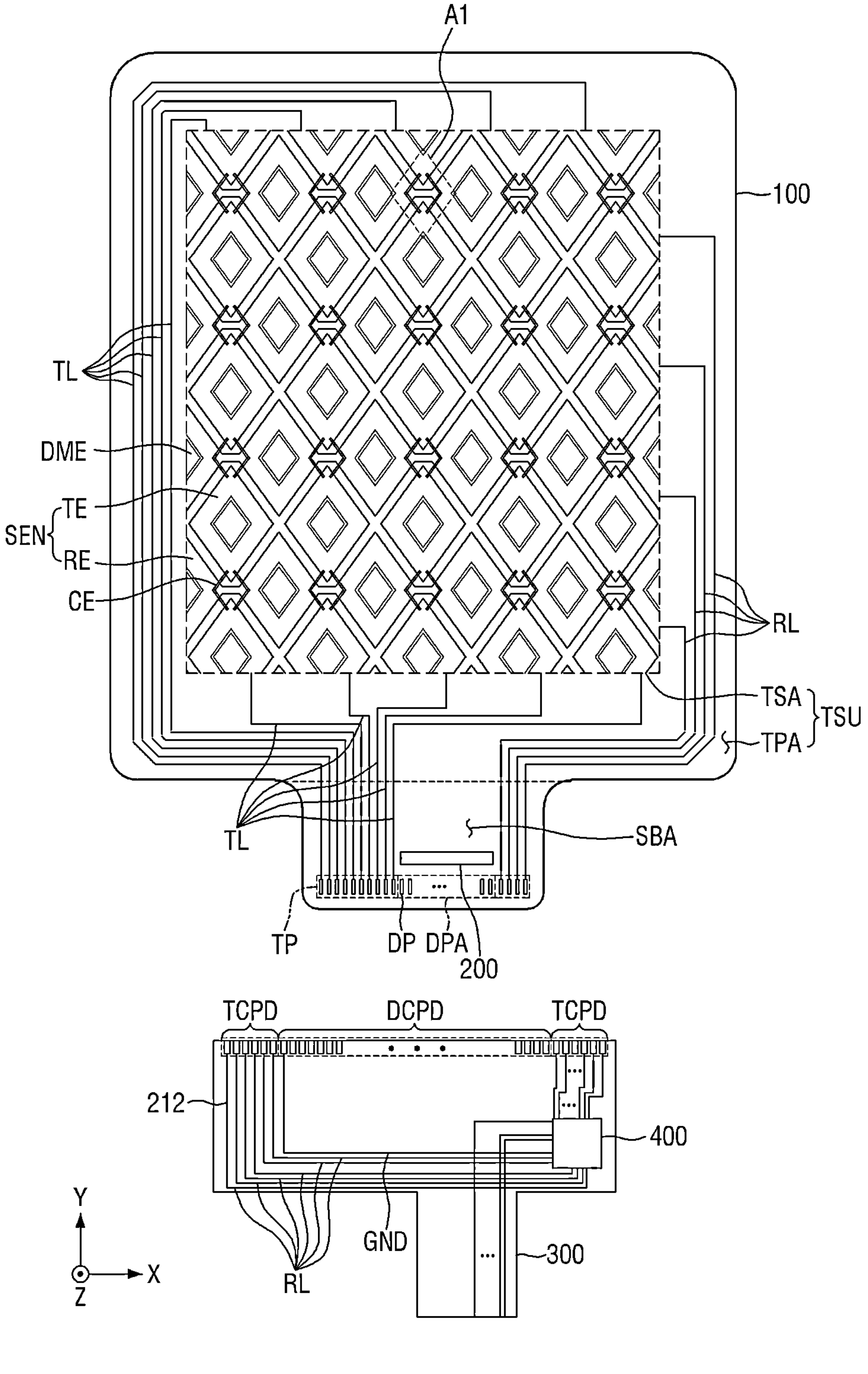
FIG. 5 is a schematic plan view showing the touch unit of the display device according to the embodiment.

The touch area TSA may include touch electrodes SEN (e.g., TE and RE in FIG. 5), touch driving lines TL (see FIG. 5), and touch sensing lines RL (see FIG. 5). The touch area TSA may detect a touch input by receiving an electrical signal Tx from the touch driver 400 disposed on the circuit board 300 through the touch driving lines TL or by sending an electrical signal Rx sensed from the sensing electrodes RE to the touch driver 400 through the touch sensing lines RL. For example, the touch driver 400 may detect a touch input by converting an analog electrical signal Rx detected by the touch area TSA into a digital signal. The touch driver 400 will be described in detail later with reference to FIG. 5.

Referring to FIG. 4, the display unit DU may include the display area DA and the non-display area NDA. The display unit DU may include sub-pixels PX, and gate lines GL and data lines DL connected (e.g., electrically connected) to the sub-pixels PX.

The gate lines GL may supply the gate signals received from the gate driver 210 to the sub-pixels PX. The gate lines GL may extend in the first direction X and may be spaced apart from one another in the second direction Y intersecting the first direction X.

The data lines DL may supply the output data signals DR, DG and DB and the data signals received from the display driver 200 to the sub-pixels PX. The data lines DL may extend in the second direction Y and may be spaced apart from one another in the first direction X.

The non-display area NDA may surround the display area DA. For example, the non-display area NDA may include the gate driver 210 for applying gate signals to the scan lines SL, fan-out lines FOL for connecting the data lines DL with the display driver 200, and display pads DP connected (e.g., electrically connected) to circuit board 300.

The display driver 200 may supply the gate driver control signal GCS to the gate driver 210 through a gate control line GCL. The gate driver 210 may generate gate signals based on the gate driver control signal GCS, and may sequentially supply the gate signals to the gate lines GL in a selected order.

The display driver 200 may supply a first supply voltage to a first voltage line VL and a second supply voltage to a second voltage line through the data driver 230. Each of the sub-pixels PX may receive the first supply voltage through the first voltage line VL and may receive the second supply voltage through the second voltage line. The first supply voltage may be a reference high-level voltage, and the second supply voltage may be a voltage lower than the first supply voltage.

The display pad area DPA and the touch peripheral area (or touch pad area) TPA may be disposed at an edge portion of the display panel 100. The display pad area DPA may include display pads DP. The display pads DP may be connected (e.g., electrically connected) to a main processor through the circuit board 300. The display pads DP may be connected (e.g., electrically connected) to the circuit board 300 to receive digital video data and may supply the digital video data to the display driver 200.

FIG. 5 is a schematic plan view showing the touch unit of the display device according to the embodiment.

Referring to FIG. 5, the touch unit TSU may include the touch area TSA that senses a user's touch, and a touch peripheral area TPA disposed around the touch area TSA. The touch area TSA may overlap the display area DA of the display panel 100, and the touch peripheral area TPA may overlap the non-display area NDA of the display panel 100.

The touch unit TSU may include driving electrodes TE, sensing electrodes RE, touch driving lines TL, and touch sensing lines RL.

The circuit board 300 may include first circuit pads DCPD connected (e.g., electrically connected) to the display pads DP of the display panel 100, second circuit pads TCPD connected (e.g., electrically connected) to the touch pads TP of the display panel 100, and touch circuit lines 212 connecting (e.g., electrically connecting) the second circuit pads TCPD to the touch driver 400. The driving electrodes TE and the sensing electrodes RE of the touch area TSA may be connected (e.g., electrically connected) to the touch driver 400 of the circuit board 300. The touch area TSA may receive an electrical signal from the touch driver 400 disposed on the circuit board 300 through the touch driving lines TL and the touch sensing lines RL or may send an electrical signal sensed from the driving electrode TE or the sensing electrodes RE to the touch driver 400 through the touch driving lines TL and the touch sensing lines RL.

The driving electrodes TE may be arranged in the first direction X and in the second direction Y. The driving electrodes TE may be spaced apart from one another in the first direction X and in the second direction Y. The driving electrodes TE adjacent to one another in the second direction Y may be connected (e.g., electrically connected) through bridge electrodes CE.

The driving electrodes TE may be connected (e.g., electrically connected) to the touch pads TP through the touch driving lines TL. Some of the touch driving lines TL may pass the lower side of the touch peripheral area TPA and may extend to the touch pads TP. Some others of the touch driving lines TL may pass the upper side, the left side and the lower side of the touch peripheral area TPA and may extend to the touch pads TP. The touch pads TP may be connected (e.g., electrically connected) to the touch driver 400 through the circuit board 300.

The display pad area DPA and the touch peripheral area TPA may be disposed at the edge portion of the subsidiary area SBA of the display panel 100. The display pad area DPA and the touch peripheral area TPA may be connected (e.g., electrically connected) to the circuit board 300 by using a low-resistance and high-reliability material such as an anisotropic conductive film.

The sensing electrodes RE may extend in the first direction X and may be spaced apart from one another in the second direction Y. The sensing electrodes RE may be arranged in the first direction X and the second direction Y, and the sensing electrodes RE adjacent to one another in the first direction X may be connected (e.g., electrically connected) through connecting portions.

The sensing electrodes RE may be connected (e.g., electrically connected) to the touch pads TP through the touch sensing lines RL. For example, the sensing electrodes RE disposed on the right side of the touch area TSA may be connected (e.g., electrically connected) to the touch pads TP through touch sensing lines RL. The touch sensing lines RL may extend to the touch pads TP via the right side and the lower side of the touch peripheral area TPA. The touch pads TP may be connected (e.g., electrically connected) to the touch driver 400 through the circuit board 300.

The driving electrodes TE and the sensing electrodes RE may include a planar pattern formed of a transparent conductive layer or may include a mesh pattern formed of an opaque metal along regions where the light-emitting diodes ED are not disposed, and thus they may not hinder the progress (or may not obstruct the passage) of lights emitted from the display area DA.

A touch driving signal may be applied from the touch driver 400 to each of the driving electrodes TE through one of the touch driving lines TL. In case that a touch driving signal is applied to the driving electrodes TE, mutual capacitance may be formed between adjacent driving electrodes TE and sensing electrodes RE. In case that there is a touch input from the outside, the mutual capacitance between adjacent driving electrodes TE and sensing electrodes RE may vary. A change in mutual capacitance between adjacent driving electrodes TE and sensing electrodes RE may be transferred to the touch driver 400 through touch sensing lines RL. Accordingly, the touch driver 400 may determine whether there is a touch input and may calculate touch input coordinates of the position. Touch may be sensed by mutual capacitance sensing, but embodiments are not limited thereto.

In FIG. 5, a ground line GND may be formed on the circuit board 300.

Dummy electrodes (or dummy patterns) DME are also shown in FIG. 5. Driving electrodes TE, sensing electrodes RE and dummy electrodes DME may be disposed on the same layer and may be spaced apart from one another.

Figure 6:
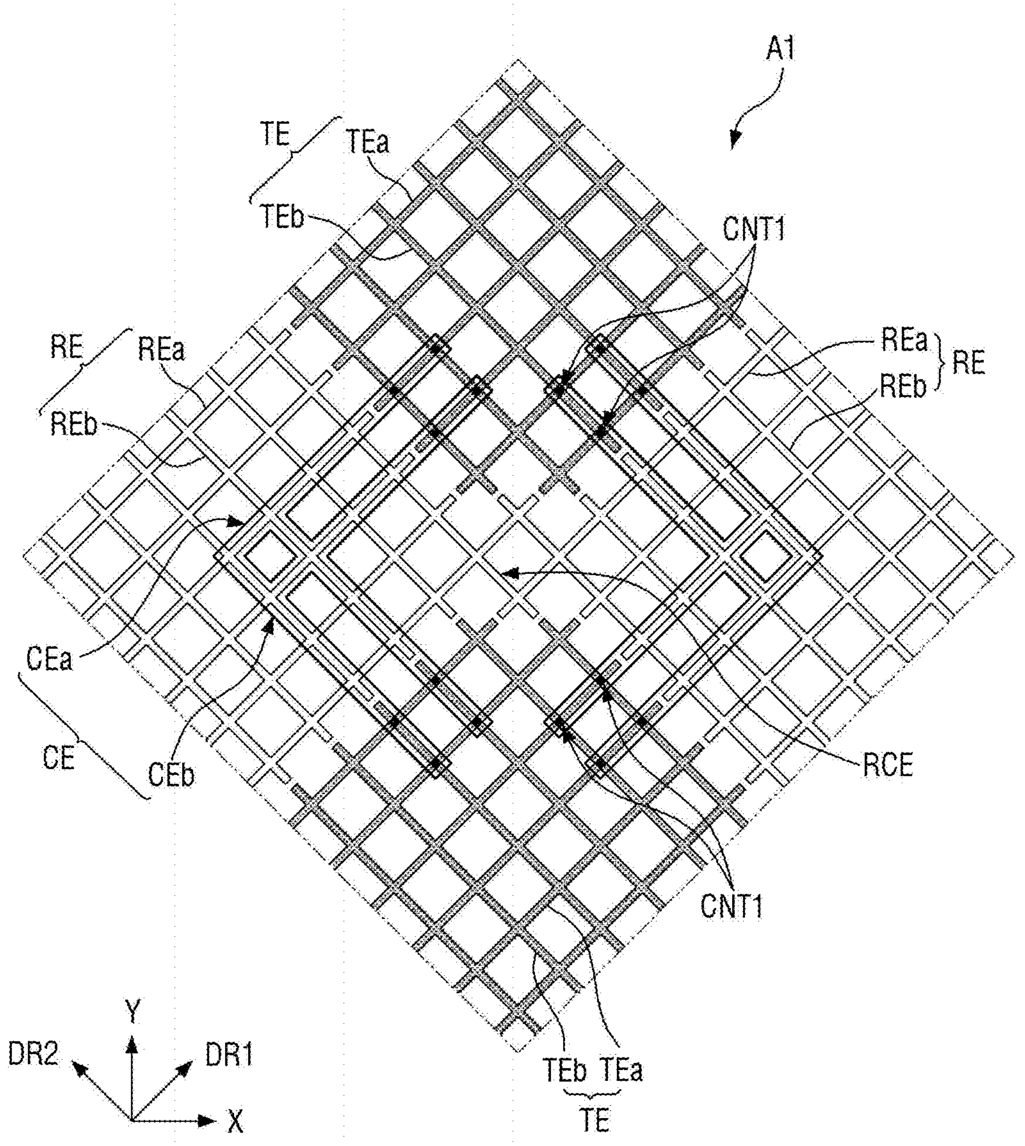
FIG. 6 is an enlarged schematic view of area A1 of FIG. 5.
Figure 7:
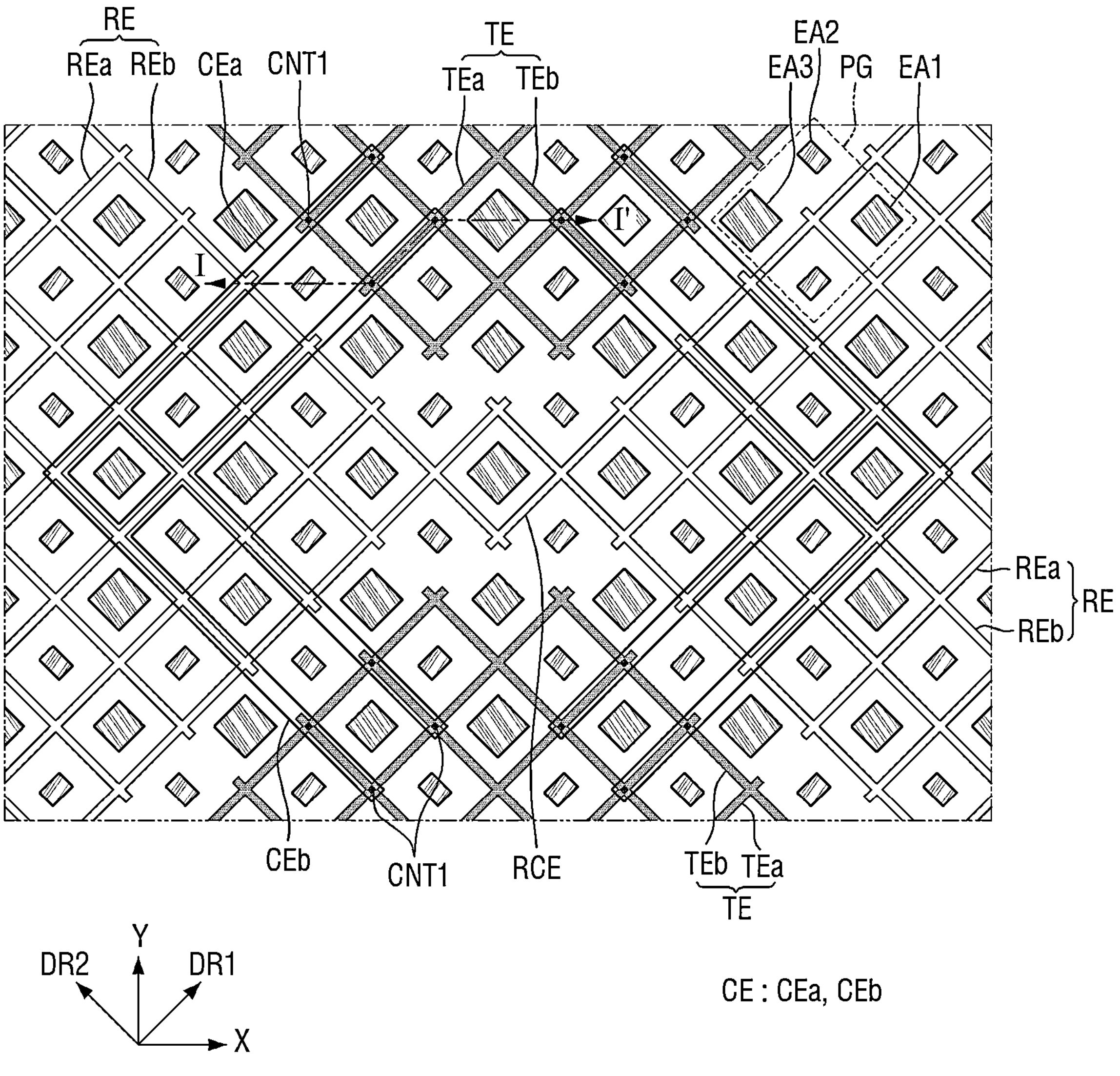
FIG. 7 is an enlarged schematic view showing a part of a display device according to an embodiment.

FIG. 6 is an enlarged schematic view of area A1 of FIG. 5. FIG. 7 is an enlarged schematic view showing a part of a display device according to an embodiment.

Referring to FIGS. 6 and 7, the driving electrodes TE may be arranged in the first direction X and in the second direction Y. The driving electrodes TE may be spaced apart from one another in the first direction X and in the second direction Y. The driving electrodes TE adjacent to one another in the second direction Y may be connected (e.g., electrically connected) through bridge electrodes CE.

The sensing electrodes RE may extend in the first direction X and may be spaced apart from one another in the second direction Y. The sensing electrodes RE may be arranged in the first direction X and the second direction Y, and the sensing electrodes RE adjacent to one another in the first direction X may be connected (e.g., electrically connected) through connecting portions RCE. For example, the connecting portions RCE of the sensing electrodes RE may traverse between the driving electrodes TE adjacent to each other.

The bridge electrodes CE may be disposed on a different layer from the driving electrodes TE and the sensing electrodes RE. Each of the bridge electrodes CE may include a first portion CEa and a second portion CEb. For example, the second portion CEb of the bridge electrode CE may be connected (e.g., electrically connected) to the driving electrode TE disposed on a side through a first contact hole CNT1 and may extend in the direction DR2. The first portion CEa of the bridge electrode CE may be bent from the second portion CEb where it overlaps the sensing electrode RE to extend in a direction DR1, and may be connected (e.g., electrically connected) to the driving electrode TE disposed on the other side through a first contact hole CNT1. For example, the direction DR1 may refer to the direction between the first direction X and the second direction Y, and the direction DR2 may refer to the direction intersecting the direction DR1. For example, each of the bridge electrodes CE may connect (e.g., electrically connect) between the driving electrodes TE adjacent to each other in the second direction Y.

According to the embodiment, the driving electrodes TE, the sensing electrodes RE and the dummy electrodes DME (see FIG. 5) may be formed in a mesh pattern or a net pattern when viewed from the top (or in plan view). The driving electrodes TE, the sensing electrodes RE and the dummy electrodes DME (see FIG. 5) may not overlap the first to third emission areas EA1, EA2, and EA3 of the pixels PX. The bridge electrodes CE may not overlap the first to third emission areas EA1, EA2 and EA3. Accordingly, the display device 10 may prevent the brightness of the light exiting from the emission areas EA1, EA2 and EA3 from being lowered by the touch unit TSU.

Each of the driving electrodes TE may include a first portion TEa extended in the direction DR1 and a second portion TEb extended in the direction DR2. Each of the sensing electrodes RE may include a first portion REa extended in the direction DR1 and a second portion REb extended in the direction DR2.

According to another embodiment, the driving electrodes TE, the sensing electrodes RE and the dummy electrodes DME (see FIG. 5) may be formed as whole surfaces when viewed from the top (or in plan view), instead of a mesh pattern or a net pattern. In this instance, the driving electrodes TE, the sensing electrodes RE and the dummy electrodes DME (see FIG. 5) may include a transparent conductive material having high light transmittance such as indium tin oxide (ITO) and indium zinc oxide (IZO).

The pixels PX may include first to third sub-pixels. The first to third sub-pixels may include first to third light emission areas EA1, EA2 and EA3, respectively. For example, the first emission area EA1 may emit light of a first color or red light, the second emission area EA2 may emit light of a second color or green light, and the third emission area EA3 may emit light of a third color or blue light. It is, however, to be understood that embodiments are not limited thereto.

A single pixel PX may include one first emission area EA1, two second emission areas EA2 and one third emission area EA3 to represent (or depict) black-and-white/grayscale levels. Accordingly, black-and-white/grayscale levels may be represented (or depicted) by a combination of light emitted from one first emission area EA1, lights emitted from two second emission areas EA2, and light emitted from one third emission areas EA3.

Figure 8:
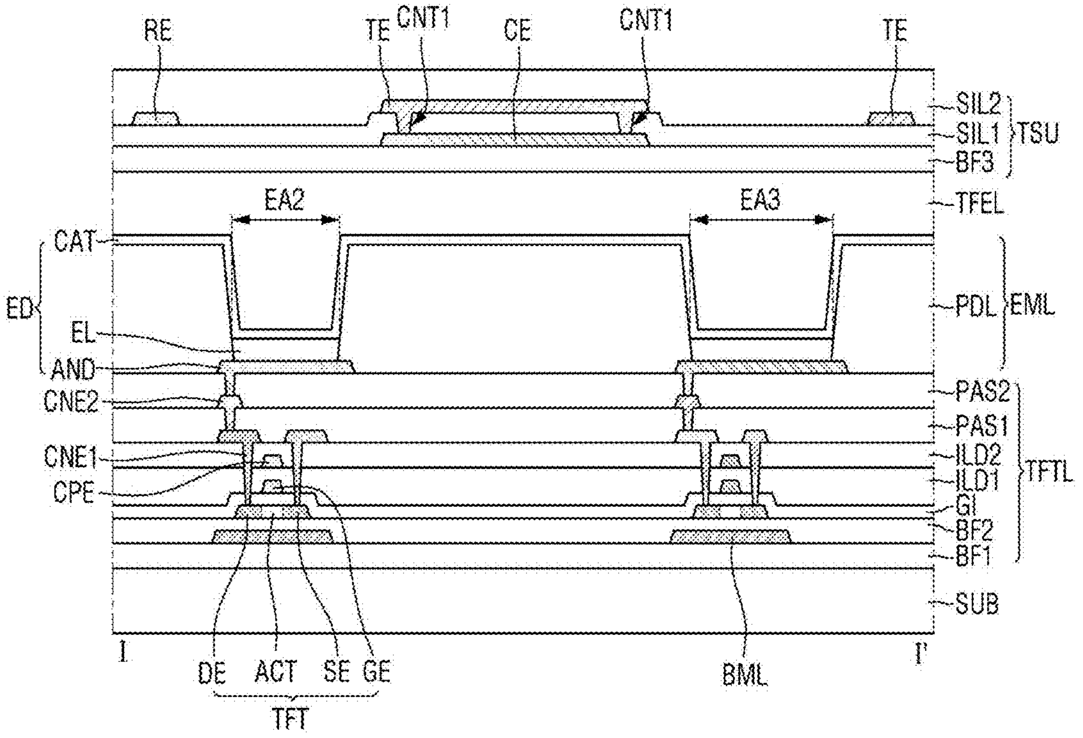
FIG. 8 is a schematic cross-sectional view of the display device according to the embodiment, taken along line I-I' of FIG. 7.

FIG. 8 is a schematic cross-sectional view, taken along line I-I' of FIG. 7.

Referring to FIG. 8, the display panel 100 may include the display unit DU and the touch unit TSU. The display unit DU may include a substrate SUB, a thin-film transistor layer TFTL, an emission material layer EML and an encapsulation layer TFEL.

The substrate SUB may support the display panel 100. The substrate SUB may be a base substrate or a base member and may be made of an insulating material such as a polymer resin. For example, the substrate SUB may be a flexible substrate that is bendable, foldable, or rollable. As another example, the substrate SUB may include a flexible material and a rigid material.

The thin-film transistor layer TFTL may include first and second buffer layers BF1 and BF2, thin-film transistors TFT, a gate insulator GI, a first interlayer dielectric layer ILD1, capacitor electrodes CPE, a second interlayer dielectric layer ILD2, first connection electrodes CNE1, a first passivation layer PAS1, second connection electrodes CNE2, and a second passivation layer PAS2.

The first buffer layer BF1 may be disposed on the substrate SUB. The first buffer layer BF1 may include an inorganic film capable of preventing permeation of air or moisture. For example, the first buffer layer BF1 may include inorganic films stacked on one another alternately.

The light-blocking layer BML may be disposed on the first buffer layer BF1. For example, the light-blocking layer BML may be made up of a single layer or multiple layers of one of molybdenum (Mo), aluminum (Al), chromium (Cr), gold (Au), titanium (Ti), nickel (Ni), neodymium (Nd) and copper (Cu) or an alloy thereof. For another example, the light-blocking layer BML may be an organic layer including a black pigment.

The second buffer layer BF2 may cover the first buffer layer BF1 and the light-blocking layer BML. The second buffer layer BF2 may include an inorganic film capable of preventing permeation of air or moisture. For example, the second buffer layer BF2 may include inorganic films stacked on one another alternately.

The thin-film transistor TFT may be disposed on the second buffer layer BF2 and may form a pixel circuit of each of pixels. For example, the thin-film transistor TFT may be a driving transistor or a switching transistor of the pixel circuit. The thin-film transistor TFT may include a semiconductor region ACT, a gate electrode GE, a source electrode SE, and a drain electrode DE.

The semiconductor region ACT, the source electrode SE and the drain electrode DE may be disposed on the second buffer layer BF2. The semiconductor region ACT may overlap the gate electrode GE in the thickness direction and may be insulated from the gate electrode GE by the gate insulator GI. The source electrode SE and the drain electrode DE may be formed by converting the material of the semiconductor region ACT into a conductor.

The gate electrode GE may be disposed on the gate insulator GI. The gate electrode GE may overlap the semiconductor region ACT with the gate insulator GI interposed therebetween.

The gate insulator GI may be disposed on the semiconductor region ACT, the source electrode SE and the drain electrode DE. For example, the gate insulator GI may cover the semiconductor region ACT, the source electrode SE, the drain electrode DE and the second buffer layer BF2, and may insulate the semiconductor region ACT from the gate electrode GE. The gate insulator GI may include a contact hole through which the first connection electrode CNE1 passes.

The first interlayer dielectric layer ILD1 may cover the gate electrode GE and the gate insulator GI. The first interlayer dielectric layer ILD1 may include a contact hole through which the first connection electrode CNE1 passes. The contact hole of the first interlayer dielectric layer ILD1 may be connected to the contact hole of the gate insulator GI and the contact hole of the second interlayer dielectric layer ILD2.

The capacitor electrode CPE may be disposed on the first interlayer dielectric layer ILD1. The capacitor electrode CPE may overlap the gate electrode GE in the third direction (e.g., z-axis direction).

The second interlayer dielectric layer ILD2 may cover the capacitor electrode CPE and the first interlayer dielectric layer ILD1. The second interlayer dielectric layer ILD2 may include a contact hole through which the first connection electrode CNE1 passes. The contact hole of the second interlayer dielectric layer ILD2 may be connected to the contact hole of the first interlayer dielectric layer ILD1 and the contact hole of the gate insulator GI.

The first connection electrode CNE1 may be disposed on the second interlayer dielectric layer ILD2. The first connection electrode CNE1 may connect (e.g., electrically connect) the drain electrode DE of the thin-film transistor TFT to the second connection electrode CNE2. The first connection electrode CNE1 may be inserted into a contact hole formed in the second interlayer dielectric layer ILD2, the first interlayer dielectric layer ILD1, and the gate insulator GI to be in contact with the drain electrode DE of the thin-film transistor TFT.

The first passivation layer PAS1 may cover the first connection electrode CNE1 and the second interlayer dielectric layer ILD2. The first passivation layer PAS1 may protect the thin-film transistor TFT. The first passivation layer PAS1 may include a contact hole through which the second connection electrode CNE2 passes.

The second connection electrode CNE2 may be disposed on the first passivation layer PAS1. The second connection electrode CNE2 may connect (e.g., electrically connect) the first connection electrode CNE1 to a first electrode AND of a light-emitting diode (or light-emitting element) ED. The second connection electrode CNE2 may be inserted into a contact hole formed in the first passivation layer PAS1 to be in contact with the first connection electrode CNE1.

The second passivation layer PAS2 may cover the second connection electrode CNE2 and the first passivation layer PAS1. The second passivation layer PAS2 may include a contact hole through which the first electrode AND of the light-emitting diode ED passes.

The emission material layer EML may be disposed on the thin-film transistor layer TFTL. The emission material layer EML may include a light-emitting diode ED and a pixel-defining layer PDL. The light-emitting diode ED may include a first electrode AND, an emissive layer EL, and a second electrode CAT.

The first electrode AND may be disposed on the second passivation layer PAS2. The first electrode AND may overlap one of the first to third emission areas EA1, EA2 and EA3 defined by the pixel-defining layer PDL. The first electrode AND may be connected (e.g., electrically connected) to the drain electrode DE of the thin-film transistor TFT through the first and second connection electrodes CNE1 and CNE2.

The emissive layer EL may be disposed on the first electrode AND. For example, the emissive layer EL may be an organic emissive layer made of an organic material, but embodiments are not limited thereto. In case that the emissive layer EL is an organic emissive layer, in case that the thin-film transistor applies a reference voltage to the first electrode AND of the light-emitting diode ED and the second electrode CAT of the light-emitting diode ED receives a common voltage or cathode voltage, the holes and electrons may move to the organic emissive layer EL through the hole transporting layer and the electron transporting layer, respectively, and they combine in the organic layer to emit light.

The second electrode CAT may be disposed on the emissive layer EL. For example, the second electrode CAT may be implemented as an electrode that commonly covers all the pixels, instead of being disposed as a separated electrode for each of the pixels. For example, the second electrode CAT may be disposed on the emissive layer EL in the first to third emission areas EA1, EA2 and EA3, and may be disposed on the pixel-defining layer PDL in the other areas than the first to third emission areas EA1, EA2 and EA3.

The pixel-defining layer PDL may define first to third emission areas EA1, EA2 and EA3. The pixel-defining layer PDL may separate and insulate the first electrode AND of one of the light-emitting diodes ED from the anode electrode of another one of the light-emitting diodes ED.

The encapsulation layer TFEL may be disposed on the second electrode CAT to cover the light-emitting diodes ED. The encapsulation layer TFEL may include at least one inorganic layer to prevent permeation of oxygen or moisture into the emission material layer EML. The encapsulation layer TFEL may include at least one organic layer to protect the emission material layer EML from foreign substances such as dust.

The touch unit TSU may be disposed on the encapsulation layer TFEL. The touch unit TSU may include a third buffer layer BF3, a bridge electrode CE, a first insulating layer SIL1, a driving electrode TE, a sensing electrode RE, and a second insulating layer SIL2.

The third buffer layer BF3 may be disposed on the encapsulation layer TFEL. The third buffer layer BF3 may be insulating and may have optical functions. The third buffer layer BF3 may include at least one inorganic layer. In another example, the third buffer layer BF3 may be eliminated.

The bridge electrode CE may be disposed on the third buffer layer BF3. The bridge electrode CE may be disposed in a different layer from the driving electrodes TE and the sensing electrodes RE, and may connect (e.g., electrically connect) between the driving electrodes TE adjacent to each other in the second direction (e.g., the second direction Y in FIG. 7). For example, the bridge electrode CE may be made up of a single layer of molybdenum (Mo), titanium (Ti), copper (Cu) or aluminum (Al), or may be made up of a stack structure of aluminum and titanium (Ti/Al/Ti), a stack structure of aluminum and ITO (ITO/Al/ITO), an APC alloy and a stack structure of an APC alloy and ITO (ITO/APC/ITO).

The first insulating layer SIL1 may cover the bridge electrode CE and the third buffer layer BF3. The first insulating layer SIL1 may have insulating and optical functionalities. For example, the first insulating layer SIL1 may be formed of an inorganic layer, e.g., a silicon nitride layer, a silicon oxynitride layer, a silicon oxide layer, a titanium oxide layer, or an aluminum oxide layer.

The driving electrodes TE and the sensing electrodes RE may be disposed on the first insulating layer SIL1. Each of the driving electrodes TE and the sensing electrodes RE may overlap none of the first to third emission areas EA1, EA2 and EA3. Each of the driving electrodes TE and the sensing electrodes RE may be made up of a single layer of molybdenum (Mo), titanium (Ti), copper (Cu) or aluminum (Al), or may be made up of a stack structure of aluminum and titanium (Ti/Al/Ti), a stack structure of aluminum and ITO (ITO/Al/ITO), an APC alloy, or a stack structure of an APC alloy and ITO (ITO/APC/ITO).

The second insulating layer SIL2 may cover the driving electrode TE, the sensing electrode RE and the first insulating layer SIL1. The second insulating layer SIL2 may have insulating features and optical features. The second insulating layer SIL2 may be made of one of the above-listed materials as the material of the first insulating layer SIL1.

Although the bridge electrode CE is formed in the layer under the driving electrode TE and the sensing electrode RE in FIG. 8, embodiments are not limited thereto. For example, the bridge electrode CE may be formed in the layer above the driving electrode TE and the sensing electrode RE.

Figure 9:
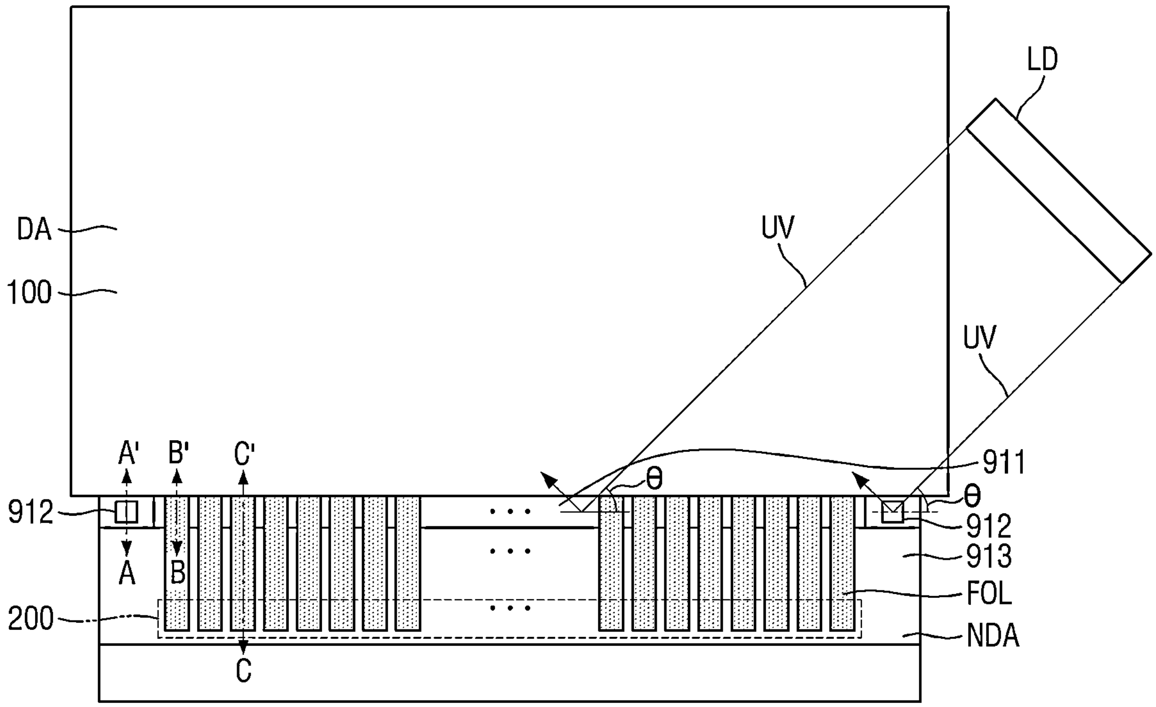
FIG. 9 is a schematic view showing a part of the outer portion of a display panel according to an embodiment.
Figure 10:
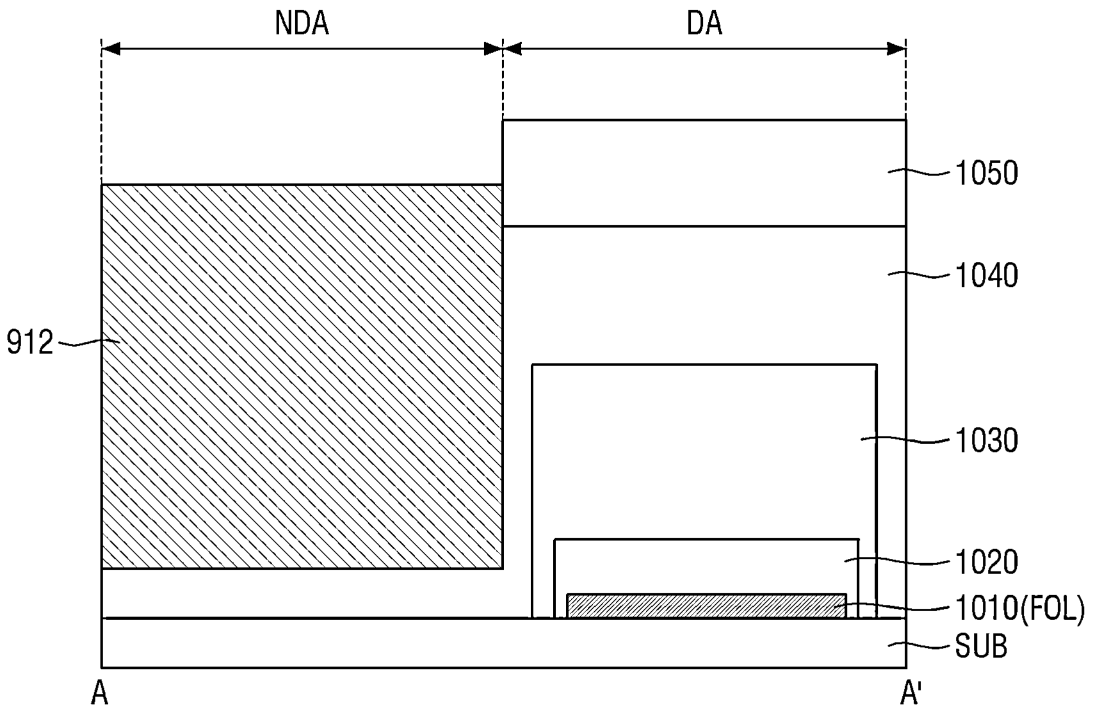
FIG. 10 is a schematic cross-sectional view taken along line A-A' of FIG. 9 illustrating a part of a dummy area of the display panel according to the embodiment.
Figure 11:
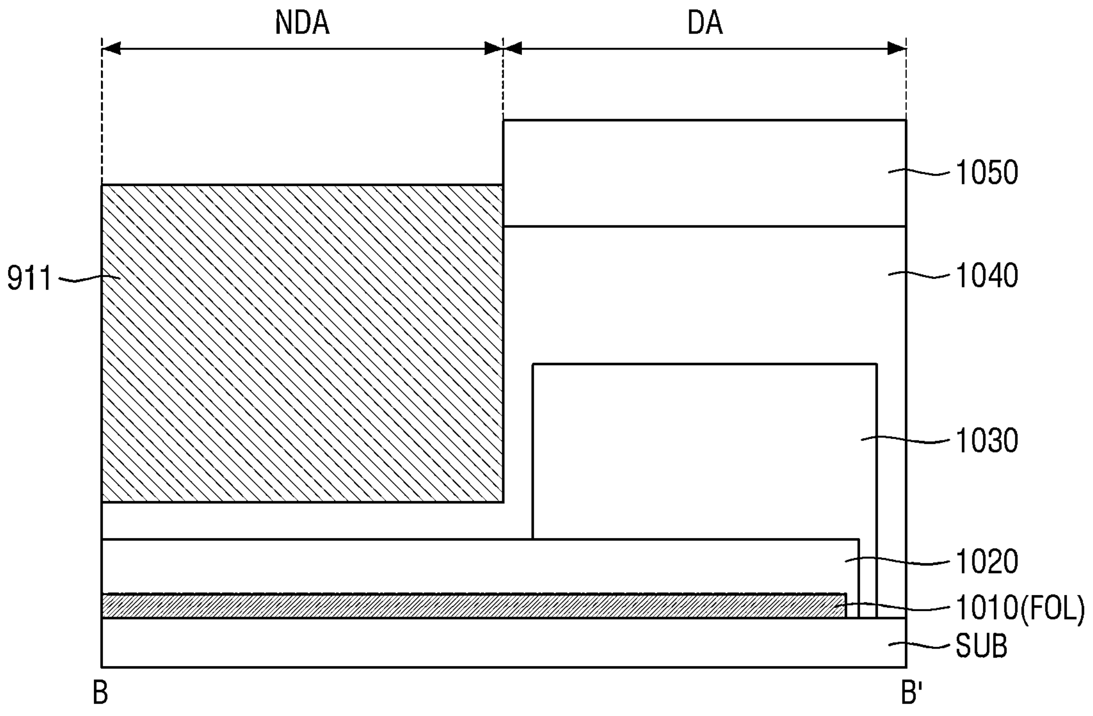
FIG. 11 is a schematic cross-sectional view taken along line B-B' of FIG. 9 illustrating a part of a boundary area disposed between an encapsulation area of an encapsulation layer and a cover area of a protective layer of the display panel according to the embodiment.
Figure 12:
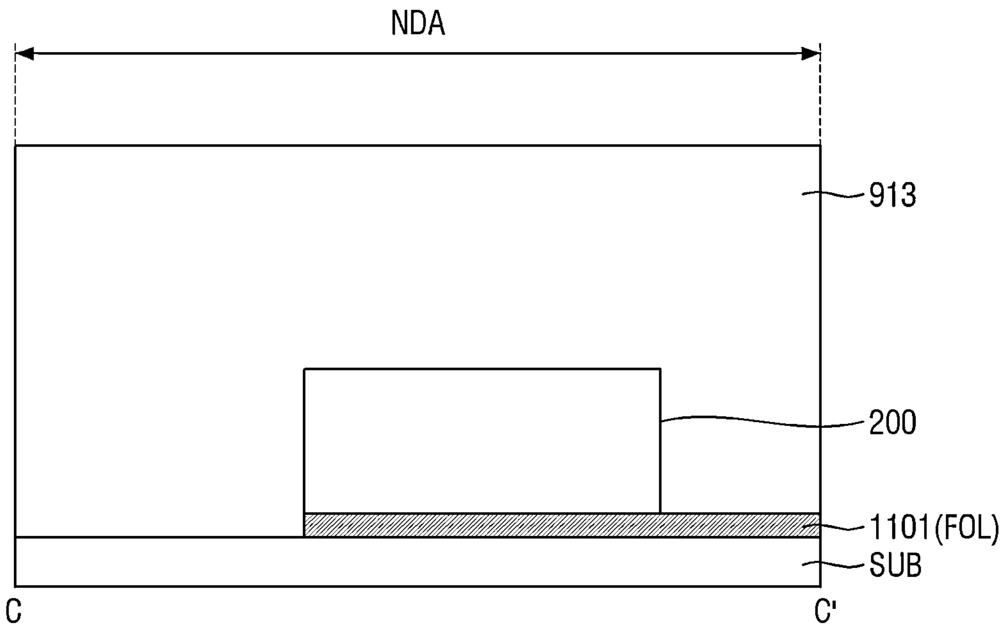
FIG. 12 is a schematic cross-sectional view taken along line C-C' of FIG. 9.

FIG. 9 is a schematic view showing a part of the outer portion of a display panel according to an embodiment. FIG. 10 is a schematic cross-sectional view of a part of a dummy area of the display panel according to the embodiment. FIG. 11 is a schematic cross-sectional view of a part of a boundary area positioned between an encapsulation area of an encapsulation layer and a cover area of a protective layer of the display panel according to an embodiment. FIG. 12 is a schematic cross-sectional view of a part of the bending area SBA of the display panel according to the embodiment. For example, FIG. 10 is a schematic cross-sectional view of the display panel shown in FIG. 9 taken along line A-A'. FIG. 11 is a schematic cross-sectional view of the display panel shown in FIG. 9 taken along line B-B'. FIG. 12 is a schematic cross-sectional view taken along line C-C' of FIG. 9.

Referring to FIGS. 9 to 11, the display panel may include the display area DA and the non-display area NDA, and may be fabricated with a substrate SUB that is bendable, foldable, or rollable as a base.

A backplane 1010, an insulating layer 1020, an organic light-emitting layer 1030, an encapsulation layer 1040 (e.g., the encapsulation layer TFEL in FIG. 8), and a polarizing film 1050 are disposed in the display area DA of the substrate SUB. The backplane 1010 may include the thin-film transistor TFT described above with reference to FIG. 8 and at least one signal line and/or at least one voltage line connected (e.g., electrically connected) to the thin-film transistor TFT.

The non-display area NDA of the substrate SUB may be positioned outside the display area DA. FIG. 9 shows a part of the non-display area NDA including a bending area (e.g., the subsidiary area SBA of FIG. 2) where a driver circuit (e.g., the display driver 200 of FIG. 2) is bonded. For example, the non-display area NDA may include a bending area SBA that is bent to overlap a part of the display area DA, where the driver circuit 200 is bonded.

According to the embodiment, the bending area SBA, which is a part of the non-display area NDA, may include a bending protective layer (BPL) area 1303 where a protective layer 913 covering the driver circuit 200 is disposed (e.g., first area), and a shielding area where a shielding resin 911 in the form of an electrical shielding resin, is applied to prevent introduction of static electricity (e.g., second area).

In case that the substrate SUB is viewed from the top (or in plan view), the shielding resin 911 in the shielding area may be disposed between the protective layer 913 in the BPL area 1303 (see FIG. 14) and the polarizing film 1050 in the display area DA.

According to an embodiment, the bending area SBA may further include a dummy area 1302 (see FIG. 14) positioned adjacent to the shielding resin 911. The dummy area 1302 may be positioned between the protective layer 913 of the BPL area 1303 and the polarizing film 1050 of the display area DA, and may be positioned adjacent to at least one side of the shielding resin 911 when the substrate SUB is viewed from the top (or in plan view).

For example, the bending area SBA may include a shielding area where fan-out lines FOL of the backplane 1010 extended from the display area DA to the driver circuit 200 and the shielding resin 911 covering the fan-out lines FOL are disposed, and a dummy area 1302 positioned at each of the end portions (e.g., opposite end portions) of the shielding area. In the dummy area 1302, a test pattern 912 may be applied.

For example, the dummy area 1302 may be defined as an area where the fan-out lines FOL is not disposed.

For example, the dummy area 1302 may be positioned at the end portions (or at least one side) of the shielding area where the shielding resin 911 is applied, and may be defined as an area where an alignment key is disposed.

For example, the dummy area 1302 may be a part of the non-display area NDA where the pixels PX are not disposed, or may be a part of the non-display area NDA that remains bent. The test pattern 912 made of substantially the same material as the shielding resin 911 is applied in the dummy area 1302. For example, the test pattern 912 may be disposed adjacent to the alignment key.

The test pattern 912 may be used as an indicator for setting optimal optical conditions in a process of inspecting whether the shielding resin 911 is properly applied (or formed). For example, the process of inspecting whether the shielding resin 911 is properly applied (or formed) may include irradiating the test pattern 912 with ultraviolet light UV according to the number of optical conditions, and determining optimal optical condition based on the ultraviolet light reflected from the test pattern 912.

The optimal optical condition may mean the condition that allows the shielding area where the shielding resin 911 is disposed to be readily distinguished from the BPL area 1303.

The optimal optical condition may mean the condition that allow the shielding area where the shielding resin 911 is disposed to be readily distinguished from the display area DA where the polarizing film 1050 is attached.

After the optimal optical condition is determined, it may be inspected whether the shielding resin 911 is properly applied (or formed) by irradiating the shielding resin 911 with ultraviolet light UV according to the determined optical condition.

In case that the shielding resin 911 is not properly applied (or formed), the irregularity (which is the opposite of uniformity) of ultraviolet light reflected from the shielding resin 911 may exceed a reference threshold value.

The inspection process according to an embodiment may include determining whether the shielding resin 911 is properly applied (or formed) according to whether the irregularity (which is the opposite of uniformity) of ultraviolet light reflected from the shielding resin 911 exceeds a specified threshold value.

Although a part of the encapsulation layer 1040 is disposed between the test pattern 912 and the substrate SUB in FIG. 10, embodiments are not limited thereto. In another example, the encapsulation layer 1040 may not be disposed between the test pattern 912 and the substrate SUB.

FIG. 10 shows an insulating layer 1020 (e.g., first and second interlayer dielectric layers ILD1 and ILD2 in FIG. 8) disposed on the backplane 1010.

Although a part of the encapsulation layer 1040 is disposed between the shielding resin 911 and the substrate SUB in FIG. 11, embodiments are not limited thereto. In another example, the encapsulation layer 1040 may not be disposed between the shielding resin 911 and the substrate SUB.

Hereinafter, a method of inspecting is the shielding resin 911 may be properly applied (or formed) using the test pattern 912 will be described in more detail in conjunction with FIGS. 13 and 14.

For example, the test pattern 912 may be referred to as a test element group (Teg) pattern or a similar term. In the following description, the test pattern 912 will be referred to as Teg 912 for convenience of illustration.

Figure 13:
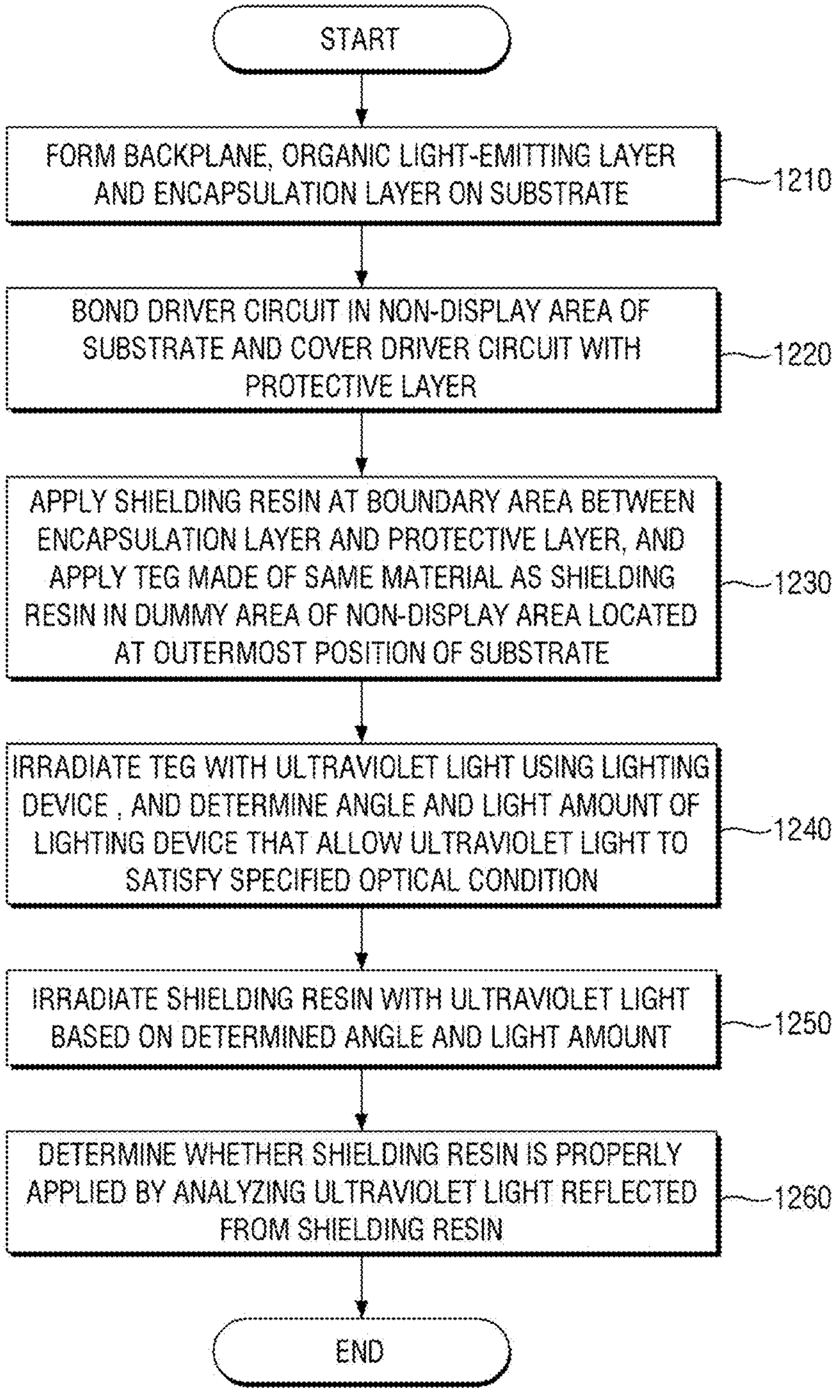
FIG. 13 is a flowchart for illustrating a method of testing a display panel according to an embodiment.

FIG. 13 is a flowchart for illustrating a method of testing a display panel according to an embodiment. FIG. 14 is a schematic view showing optical properties measured from each of the encapsulation area of the encapsulation layer 1040, the cover area of the protective layer 913, and the boundary area positioned between them.

Referring to FIG. 13, a backplane 1010, an organic light-emitting layer 1030 and an encapsulation layer 1040 are formed on a substrate SUB (step S1210). The backplane 1010, the organic light-emitting layer 1030, the encapsulation layer 1040 and a polarizing film 1050 are disposed in the display area DA of the substrate SUB. The backplane 1010 may include the thin-film transistor TFT described above with reference to FIG. 8 and at least one signal line and/or at least one voltage line connected (e.g., electrically connected) to the thin-film transistor TFT.

Referring to FIG. 13, a driver circuit 200 may be bonded to the non-display area NDA of the substrate SUB, and the driver circuit 200 may be covered with a protective layer 913 (step S1220).

The non-display area NDA of the substrate SUB may be positioned outside the display area DA. FIG. 9 shows a part of the non-display area NDA including the bending area SBA where the driver circuit 200 is bonded. For example, the non-display area NDA may include a bending area SBA that is bent to overlap a part of the display area DA, where the driver circuit 200 is bonded.

According to the embodiment, the bending area SBA, which is a part of the non-display area NDA, may include a bending protective layer (BPL) area where a protective layer 913 covering the driver circuit 200 is disposed (e.g., first area), and a shielding area where a shielding resin 911 is applied to prevent introduction of static electricity (e.g., second area).

When the substrate SUB is viewed from the top (or in plan view), the shielding resin 911 in the shielding area may be disposed between the protective layer 913 in the BPL area 1303 and the polarizing film 1050 in the display area DA.

According to an embodiment, the bending area SBA may further include a dummy area 1302 positioned adjacent to the shielding resin 911. The dummy area 1302 may be positioned between the protective layer 913 of the BPL area 1303 and the polarizing film 1050 of the display area DA, and may be positioned adjacent to at least one side of the shielding resin 911 when the substrate SUB is viewed from the top (or in plan view).

Referring to FIG. 13, a shielding resin 911 may be applied at the boundary area (e.g., shielding area) between the encapsulation layer 1040 and the protective layer 913, and a Teg 912 made of the same material as the shielding resin 911 is applied at the dummy area 1302 of the non-display area NDA positioned at the outermost position of the substrate SUB (step S1230).

The dummy area 1302 may be defined as an area where the fan-out lines FOL is not disposed. The dummy area 1302 may be defined as an area positioned at the end portions (or at least one side) of the shielding area where the shielding resin 911 is applied. The dummy area 1302 may be a part of the non-display area NDA where the pixels PX are not disposed, and may be a part of the non-display area NDA that remains bent. The test pattern 912 made of substantially the same material as the shielding resin 911 may be applied in the dummy area 1302.

Referring to FIG. 13, ultraviolet light UV may be irradiated to the Teg 912 using a lighting device LD, and the angle Θ and the light amount of the lighting device LD may be determined so that the ultraviolet light reflected from the Teg 912 may satisfy specified optical conditions (step S1240).

According to an embodiment, determining the angle Θ and the light amount of the lighting device LD that satisfies specified optical conditions may include the following steps:

Initially, the number of optical conditions may be set as combinations of the number of angle conditions related to the angle Θ of the lighting device LD and the number of light amount conditions related to the light amount of the lighting device LD.

Referring to Table 1, the number of angle conditions related to the angle Θ of the lighting device LD may be set in a range of about 10 degrees to about 30 degrees. The number of light amount conditions related to the light amount of the lighting device LD may be set in the range of about 10 W to about 30 W.

TABLE 1

| | Brightness | | | | |
|---|---|---|---|---|---|
| Angle | 10 W | 15 W | 20 W | 25 W | 30 W |
| 10 Degrees | C1 | C2 | C3 | C4 | C5 |
| 15 Degrees | C6 | C7 | C8 | C9 | C10 |
| 20 Degrees | C11 | C12 | C13 | C14 | C15 |
| 25 Degrees | C16 | C17 | C18 | C19 | C20 |
| 30 Degrees | C21 | C22 | C23 | C24 | C25 |

Although 10 degrees, 15 degrees, 20 degrees, 25 degrees and 30 degrees are mentioned as the angle conditions related to the angle Θ of the lighting device LD in Table 1, embodiments are not limited thereto.

Although 10 W, 15 W, 20 W, 25 W and 30 W are mentioned as the light amount conditions related to the light amount of the lighting device LD in Table 1, embodiments are not limited thereto.

Although 25 optical conditions C1 to C25 are mentioned as the combinations of the angles Θ and the light amounts of the lighting device LD in Table 1, embodiments are not limited thereto.

Subsequently, ultraviolet light UV may be irradiated to the substrate SUB for each of the optical conditions C1 to C25, such that the first reflected light reflected from the polarizing film 1050, the second reflected light reflected from the test pattern 912, and the third reflected light reflected from the protective layer 913 are measured. Subsequently, the average of the first reflected light and the third reflected light may be calculated, and the deviation between the average and the second reflected light may be calculated. The process of calculating the deviation of the second reflected light may be sequentially performed for each of the optical conditions C1 to C25. For example, the process of calculating the deviation of the second reflected light may be performed for each of the 25 optical conditions C1 to C25 shown in Table 1.

Figure 14:
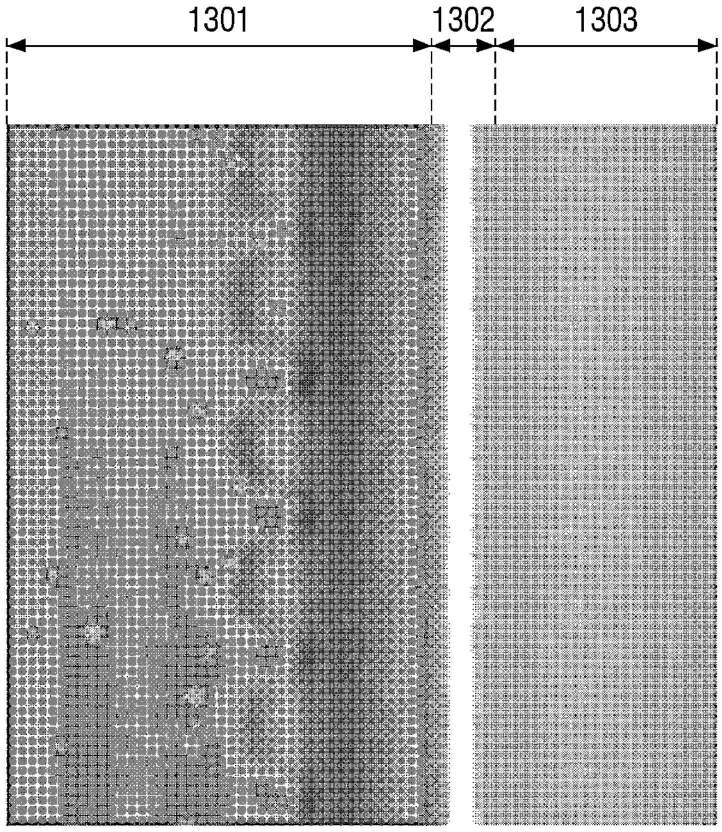
FIG. 14 is a schematic view showing optical properties measured from each of an encapsulation area of an encapsulation layer, a cover area of a protective layer, and a boundary area disposed between them.

FIG. 14 shows an example in which the first reflected light reflected from a border 1301 of the display area where the polarizing film 1050 is positioned, the second reflected light reflected from the test pattern 912 in the dummy area, and the third reflected light reflected from the protective layer 913 in the BPL area 1303 are measured.

For example, the optical condition with the smallest deviation (or smallest irregularity) between the average of the first reflected light and the third reflected light and the second reflected light may be selected from among the optical conditions.

The optical condition with the smallest deviation between the average of the first reflected light and the third reflected light and the second reflected light means that the optical condition is the optimal optical condition that allows the shielding area where the shielding resin 911 is disposed to be readily distinguished from the BPL area 1303.

The optical condition with the smallest deviation between the average of the first reflected light and the third reflected light and the second reflected light means that the optical condition is the optimal optical condition that allows the shielding area where the shielding resin 911 is disposed to be readily distinguished from the display area DA where the polarizing film 1050 is attached.

After the optimal optical condition is determined, it may be inspected whether that the shielding resin 911 is properly applied (or formed) by irradiating the shielding resin 911 with ultraviolet light UV according to the reference optical condition. In case that the shielding resin 911 is not properly applied (or formed), the irregularity (which is the opposite of uniformity) of ultraviolet light reflected from the shielding resin 911 may exceed a reference threshold value.

According to an embodiment, the determining the angle Θ and the light amount of the lighting device LD that satisfies the specified optical condition may be performed for each wafer lot, which is fabricated under the same conditions. According to the embodiment, the optimal optical condition for inspecting whether the shielding resin 911 is properly applied (or formed) may be set for each wafer lot, so that the reliability of the inspection process may be increased.

According to an embodiment, the determining the angle Θ and the light amount of the lighting device LD that satisfies the specified optical condition may be performed for each batch, which is fabricated under the same conditions. According to the embodiment, the optimal optical condition for inspecting whether the shielding resin 911 may be properly applied (or formed) is set for each batch, so that the reliability of the inspection process may be increased.

According to an embodiment, the determining the angle Θ and the light amount of the lighting device LD that satisfies the specified optical condition may be performed for each cell, which is fabricated under the same conditions. According to the embodiment, the optimal optical condition for inspecting whether the shielding resin 911 may be properly applied (or formed), and may be set for each cell, so that the reliability of the inspection process may be increased.

Referring to FIG. 13, ultraviolet light UV may be irradiated to the shielding resin 911 based on the determined angle Θ and light amount (step S1250). For example, once the optical condition with the smallest deviation between the average of the first reflected light and the third reflected light and the second reflected light may be selected from among the optical conditions, ultraviolet light UV may be irradiated to the shielding resin 911 based on that optical condition. In case that Condition C1 with the brightness of 10 W and the angle of 10 degrees has the smallest the deviation between the average of the reflected lights and the second reflected light among the 25 optical conditions shown in Table 1, ultraviolet light UV may be irradiated to the shielding resin 911 based on the condition where the brightness is 10 W and the angle is 10 degrees.

Referring to FIG. 13, it may be determined whether the shielding resin 911 is properly applied (or formed) by analyzing the ultraviolet light reflected from the shielding resin 911 (step S1260). Initially, the irregularity (which is the opposite of uniformity) of ultraviolet light reflected from the shielding resin 911 may be calculated. In case that the ultraviolet light reflected from the shielding resin 911 may be uniform, this means that the shielding resin 911 is uniformly applied on the substrate SUB. In case that the ultraviolet light reflected from the shielding resin 911 is not uniform, this means that the shielding resin 911 is not uniformly applied on the substrate SUB. Accordingly, in case that the irregularity (which is the opposite of uniformity) exceeds the reference threshold, it may be determined that the shielding resin 911 is not properly applied (or formed).

In concluding the detailed description, those skilled in the art will appreciate that many variations and modifications may be made to the embodiments without substantially departing from the principles of the present invention. Therefore, the disclosed embodiments of the invention are used in a generic and descriptive sense only and not for purposes of limitation.

What is claimed is:

1. A method for inspecting a display device, the method comprising:

forming a backplane, an organic light-emitting layer, an encapsulation layer, and a polarizing film in a display area of a substrate;

bonding a driver circuit to a non-display area of the substrate and covering the driver circuit by a protective layer;

applying a shielding resin to a boundary area between the polarizing film and the protective layer, and applying a test pattern made of a same material as the shielding resin to a dummy area of the non-display area disposed at an outermost position of the substrate;

irradiating the test pattern with ultraviolet light using a lighting device, and determining an angle and a light amount of the lighting device that make the ultraviolet light reflected from the test pattern to satisfy a specified optical condition;

irradiating the shielding resin with ultraviolet light based on the determined angle and the determined light amount; and determining whether the shielding resin is properly applied by analyzing ultraviolet light reflected from the shielding resin.

2. The method of claim 1, wherein the non-display area comprises a bending area that is bent to overlap the display area, wherein the driver circuit is bonded in the bending area, and the bending area comprises:

a shielding area where a plurality of fan-out lines extended from the display area to the driver circuit and the shielding resin covering the plurality of fan-out lines are disposed, and a dummy area disposed at each of end portions of the shielding area.

3. The method of claim 2, wherein the fan-out lines are not disposed in the dummy area.

4. The method of claim 1, wherein the determining of the angle and the light amount of the lighting device that satisfies the specified optical condition comprises:

setting a plurality of optical conditions as combinations of a plurality of angle conditions related to the angle of the lighting device and a plurality of light amount conditions related to the light amount of the lighting device;

irradiating ultraviolet light to the substrate according to each of the optical conditions, and measuring first reflected light reflected from the polarizing film, second reflected light reflected from the test pattern, and third reflected light reflected from the protective layer;

calculating an average of the first reflected light and the third reflected light, and calculating a deviation between the second reflected light and the calculated average of the first reflected light and the third reflected light; and calculating the deviation of the second reflected light according to each of the optical conditions, and determining that an optical condition with a smallest deviation of the second reflected light among the optical conditions satisfies the specified optical condition.

5. The method of claim 4, wherein the determining of the angle and the light amount of the lighting device that satisfy the specified optical condition is performed for each wafer lot, which is fabricated under same conditions.

6. The method of claim 4, wherein the determining of the angle and the light amount of the lighting device that satisfy the specified optical condition is performed for each batch, which is fabricated under same conditions.

7. The method of claim 4, wherein the determining of the angle and the light amount of the lighting device that satisfy the specified optical condition is performed for each cell, which is fabricated under same conditions.

8. The method of claim 4, wherein the angle conditions related to the angle of the lighting device are set in a range of about 10 degrees to about 30 degrees.

9. The method of claim 4, wherein the light amount conditions related to the light amount of the lighting device are set in a range of about 10 W to about 30 W.

10. The method of claim 1, wherein the determining whether the shielding resin is properly applied comprises:

calculating irregularity of ultraviolet light reflected from the shielding resin; and determining that the shielding resin is not properly applied in case that the irregularity exceeds a reference threshold value.

11. A method for inspecting a display panel, the method comprising:

forming a backplane, an organic light-emitting layer, an encapsulation layer, and a polarizing film in a display area of a substrate;

bonding a driver circuit to a non-display area of the substrate and covering the driver circuit by a protective layer;

applying a shielding resin to a boundary area between the polarizing film and the protective layer, and applying a test pattern made of a same material as the shielding resin to a dummy area of the non-display area disposed at an outermost position of the substrate;

irradiating the test pattern with ultraviolet light using a lighting device, and determining an angle and a light amount of the lighting device that make the ultraviolet light reflected from the test pattern to satisfy a specified optical condition;

irradiating the shielding resin with ultraviolet light based on the determined angle and the determined light amount; and determining whether the shielding resin is properly applied by analyzing ultraviolet light reflected from the shielding resin.

12. The method of claim 11, wherein the non-display area comprises a bending area that is bent to overlap the display area, the driver circuit is bonded in the bending area, and the bending area comprises:

a shielding area where a plurality of fan-out lines extended from the display area to the driver circuit and the shielding resin covering the plurality of fan-out lines are disposed, and a dummy area disposed at each of end portions of the shielding area.

13. The method of claim 12, wherein the fan-out lines are not disposed in the dummy area.

14. The method of claim 11, wherein the determining of the angle and the light amount of the lighting device that satisfies the specified optical condition comprises:

setting a plurality of optical conditions as combinations of a plurality of angle conditions related to the angle of the lighting device and a plurality of light amount conditions related to the light amount of the lighting device;

irradiating ultraviolet light to the substrate for each of the optical conditions, and measuring first reflected light reflected from the polarizing film, second reflected light reflected from the test pattern, and third reflected light reflected from the protective layer;

calculating an average of the first reflected light and the third reflected light, and calculating a deviation between the second reflected light and the average of the first reflected light and the third reflected light; and calculating the deviation of the second reflected light according to each of the optical conditions, and determining that an optical condition with a smallest deviation of the second reflected light among the optical conditions satisfies the specified optical condition.

15. The method of claim 14, wherein the determining of the angle and the light amount of the lighting device that satisfy the specified optical condition is performed for each wafer lot fabricated under same conditions.

16. The method of claim 14, wherein the determining of the angle and the light amount of the lighting device that satisfy the specified optical condition is performed for each batch, which is fabricated under same conditions.

17. The method of claim 14, wherein the determining of the angle and the light amount of the lighting device that satisfy the specified optical condition is performed for each cell, which is fabricated under same conditions.

18. The method of claim 14, wherein the angle conditions related to the angle of the lighting device are set in a range of about 10 degrees to about 30 degrees.

19. The method of claim 14, wherein the light amount conditions related to the light amount of the lighting device are set in a range of about 10 W to about 30 W.

20. The method of claim 11, wherein the determining whether the shielding resin is properly applied comprises:

calculating irregularity of ultraviolet light reflected from the shielding resin; and determining that the shielding resin is not properly applied in case that the irregularity of the ultraviolet light exceeds a reference threshold value.

* * * * *